United States Patent [19]

Tsukamoto et al.

[11] Patent Number: 4,996,210
[45] Date of Patent: Feb. 26, 1991

[54] HETEROCYCLIC SPIRO COMPOUNDS AND METHODS FOR PREPARING THE SAME

[75] Inventors: Shin-ichi Tsukamoto; Hitoshi Nagaoka, both of Tokyo; Shinji Usuda, Ibaragi; Masatomi Harada, Saitama; Toshinari Tamura, Saitama, all of Japan

[73] Assignee: Yamanouchi Pharmaceutical Co., Ltd., Tokyo, Japan

[21] Appl. No.: 470,091

[22] Filed: Jan. 25, 1990

Related U.S. Application Data

[62] Division of Ser. No. 254,375, Oct. 5, 1988, Pat. No. 4,940,795.

[30] Foreign Application Priority Data

Oct. 5, 1987 [JP] Japan .............................. 62-252104
Nov. 12, 1987 [JP] Japan .............................. 62-286297
Apr. 5, 1988 [JP] Japan .............................. 63-84327

[51] Int. Cl.$^5$ .................. A61K 81/445; C07D 491/07
[52] U.S. Cl. ..................................... 514/278; 514/183; 514/212; 540/466; 540/543; 546/16; 546/18
[58] Field of Search .................... 546/16, 18; 540/466; 340/543; 514/278

[56] References Cited

U.S. PATENT DOCUMENTS 4,940,795  7/1990  Tsukamoto et al. .................. 546/16

Primary Examiner—Robert T. Bond
Attorney, Agent, or Firm—Burgess, Ryan & Wayne

[57] ABSTRACT

Heterocyclic spiro compounds represented by the following general formula and salts thereof

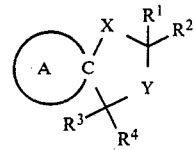

The above compounds act upon muscarinic acetylcholine receptors, thereby activating the acetylcholine nervous functions in the central nervous system.

9 Claims, No Drawings

HETEROCYCLIC SPIRO COMPOUNDS AND METHODS FOR PREPARING THE SAME

CROSS-REFERENCE

This is a division of application Ser. No. 254,375 filed Oct. 5, 1988, now U.S. Pat. No. 4,940,795.

FIELD OF THE INVENTION

This invention relates to novel heterocyclic spiro compounds and salts thereof which are useful as drugs for the prevention and treatment of diseases, particularly, caused by nervous degeneration.

BACKGROUND OF THE INVENTION

Acetylcholine is known as neurotransmitter playing an important role in cognition and mental functions in the central nervous system. Lowering of the cholin function is suggested to cause neurological and psychotic symptoms in Alzheimer's diseases, senile dementia of Alzheimer type, Huntington's chorea, Pick's diseases and senile dyskinesia. Particularly, intellectual deficits (concerning memory and cognition) are considered to result from lowered functions of acetylcholine-related central nervous system. An acetylcholinesterase inhibitor such as physostigmine, a precursor of acetylcholine such as choline and lecithin, or an acetylcholine receptor agonist such as arecoline have been used in clinical trials with these diseases [refer, for example, to S. Hirai; Clinical Neurology, 1, 200 (1983)]. However, these drugs have no therapeutical benefit, have severe side effects, and narrow range of the effective dose. Under the circumstances, there has been a demand for a new drug capable of selectively activating central cholinergic nervous system and effective for the treatment of above-mentioned diseases with little side effect.

SUMMARY OF THE INVENTION

The compounds of this invention represented by formula (I) described below are some piperidine (or piperidine with specified bridge)-tetrahydrofurane (or tetrahydrothiophene) type spiro compounds. 1-oxa-8-azaspiro[4.5]decane structure

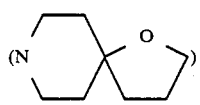

per se is known as described in, for example, Chem. Abstr. 50 13899i. However, in the compounds of this invention, there are included those of which spiro-structure portions per se are novel. Actual known similar compounds are, for example, 2,2,6,9-tetramethyl-1-oxa-8-azaspiro[4.5]decane

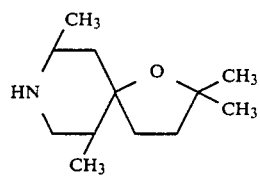

(Chem. Abstr. 70 96659r), and 6,8,9-trimethyl-4-oxo-1-oxa-8-aza-spiro[4.5]decane,

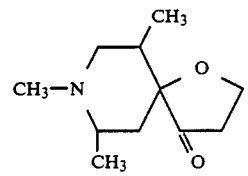

(Chem. Abstr. 74 111879r and further, 6,8,9-trimethyl-2-oxo-1-oxa-8-aza-spiro-[4.5]decane

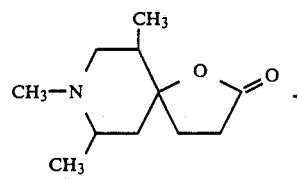

(Chem. Ab. 79 126292W), And, also, compounds of general formula

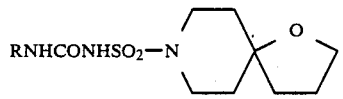

or

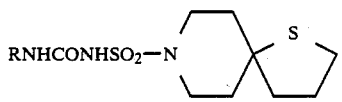

as shown in U.S. Pat. No. 3,305,556. However, the above known literatures and patents specification never disclose any use for preventing and/or treating diseases caused by the above nerve system degeneration.

DETAILED DESCRIPTION OF THE INVENTION

The compounds provided by this invention are represented by the following general formula (I):

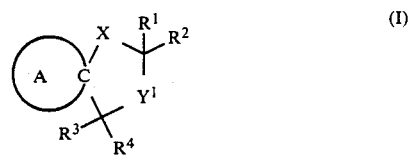

represents a piperidine ring of which the nitrogen atom may have substituent(s) selected from lower alkyl, lower alkanoyl or lower alkoxycarbonyl, and the nitrogen atom in the piperidine ring may be connected to any position carbon (which is not the common carbon atom of the spiro structure) via lower alkylene, X represents an oxygen atom or a sulfur atom, Y represents a carbonyl group

a thiocarbonyl group

a group of the formula >CH—R[5], a group of the formula

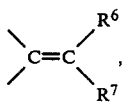

or a group of the formula

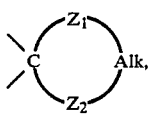

$R^1$, $R^2$ and $R^3$, which are the same or different, each represents a hydrogen atom or a lower alkyl group, $R^4$ represents a hydrogen atom, a lower alkyl group, a carboxy group, a lower alkoxycarbonyl, or a lower alkanoyl group, $R^5$ represents a halogen atom, a hydroxyl group, a marcapto group, a lower alkoxy group, a lower alkylthio group, a lower alkanoyloxy group, or a lower alkanoylthio group, $R^6$ and $R^7$, which are the same or different, each represents a hydrogen atom or a lower alkyl group, $Z^1$ and $Z^2$, which are the same or different, each represents an oxygen atom or a sulfur atom, Alk represents a lower alkylene group; or a salt of the formula (I) compound.

(Compounds)

The compounds of this invention are detailed below.

In the definition of general formulas in this specification, the term "lower" means, unless otherwise specified, a linear or branched carbon chain of 1 to 6 carbon atoms.

As illustrative examples of "lower alkyl groups", there may be mentioned methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-diemtylbutyl, 2,3-dimethylbutyl, 3,3-dimethylbutyl, 1-ethylbutyl, 2-ethylbutyl, 1,1,2-trimethylpropyl, 1,2,2-trimethypropyl, 1-ethyl-1-methylpropyl and 1-ethyl-2-methylpropyl.

As "lower alkoxy groups", may be mentioned methoxy, ethoxy, propoxy, isopropoxy, butoxy, isobutoxy, sec-butoxy, tert-butoxy, pentyloxy (amyloxy), isopentyloxy, tertpentyloxy, neopentyloxy, 2-methylbutoxy, 1,2-dimethylpropoxy, 1-ethylpropoxy and hexyloxy.

"Lower alkylthio groups" are above-mentioned lower alkoxy groups in which the oxygen atom is replaced by sulfur atom. Illustrative examples include methylthio, ethylthio, propylthio, isopropylthio, butylthio, sec-butylthio, tert-butylthio, pentylthio, neopentylthio, 2-methylbutylthio, 1,2-dimethylpropylthio and 1-ethylpropylthio.

"Lower alkoxycarbonyl groups" are groups derived from carboxyl group by esterification with a linear or branched alcohol of 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, tert-pentyloxycarbonyl, neopentyloxycarbonyl and hexyloxycarbonyl.

As "lower alkanoyl groups", may be mentioned formyl, acetyl, propionyl, butyryl, isobutyryl, valeryl, isovaleryl, pivaloyl and hexanoyl.

Illustrative examples of "lower alkanoyloxy groups" include formyloxy, acetyloxy, propionyloxy, butyryloxy, isobutyryloxy, valeryloxy, isovaleryloxy, pivaloyloxy and hexanoyloxy.

"Lower alkanoylthio groups" are above-mentioned lower alkanoyloxy groups in which the oxygen atom of the oxy radical is replaced by sulfur atom. Illustrative examples include formylthio, acetylthio, propionylthio, butyrylthio, isobutyrylthio, valerylthio, isovalerythio, pivaloylthio and hexanoylthio.

The "lower alkylene group" represented by Alk is a bivalent radical of preferably 2 to 3 carbon atoms forming a ring structure in conjunction with the radical,

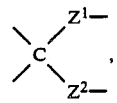

in which at least one of the carbon atoms may optionally be substituted by a lower alkyl group as defined above. Illustrative examples include ethylene, trimethylene, 1- or 2-methylethylene, 1- or 2-ethylethylene, 1- or 2-propylethylene, 1- or 2-isopropylethylene, 1- or 2-butylethylene, 1,2-dimethylethylene, 1,2-diethylethylene, 1-ethyl-2-methylethylene, 2-ethyl-1-methylethylene, 1-, 2- or 3-methyltrimethylene, 1-, 2- or 3-ethyltrimethylene, 1-, 2- or 3-propyltrimethylene, 1-, 2- or 3-isopropyltrimethylene, 1,2-, 1,3- or 2,3-diemthyltrimethylene, 1,2-, 1,3- or 2,3-diethyltrimethylene, 1,2,3-trimethyltrimethylene and 1,2,3-triethyltrimethylene.

"Halogen atom" may be any one of fluorine, chlorine, bromine and iodine.

In the terms "nitrogen atom in the piperidine ring may be connected to any position carbon (which is not the common carbon atom of the spiro structure) via lower alkylene" in the definition of the A-ring, the lower alkylene means the same meaning as defined before, and examples of such A-ring (bicyclo-type two-ring type saturated ring) are 1-azabicyclo[2,2,1]heptane ring

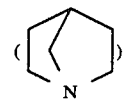

1-azabicyclo[2,2,2]octane ring

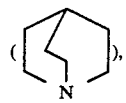

1-azabicyclo[3,2,2]nonane ring

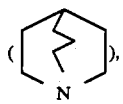

1-azabicyclo[3,1,1]heptane ring

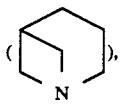

1-azabicyclo[3,2,1]octane ring

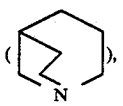

1-azabicylco[3,3,1]nonane ring

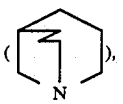

7,7-dimethyl-1-azabicyclo[2,2,1]heptane

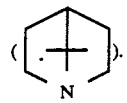

The compounds of this invention represented by the general formula (I) are capable of forming salts, and these salts are also included in this invention. Illustrative examples include acid addition salts with mineral acids, such as hydrochloric, hydrobromic, hydroiodic, sulfuric, nitric and phosphoric acids; salts with organic acids, such as formic, acetic, propionic, oxalic, malonic, succinic, fumaric, maleic, malic, tartaric, methanesulfonic and ethanesulfonic acids; and salts with acidic amino acids, such as aspartic and glutamic acids.

Some of the compounds of this invention contain asymmetric carbon atom or double bond in the molecule (depending on the type of substituent groups involved) and hence exist as a plurality of optical and geometric isomers. This invention includes all of these isomers isolated and any mixtures thereof.

(Preparative Methods)

This invention also includes preparative methods of compounds (I). These are spiro compounds constructed of a nitrogen-containing hetero ring and an oxolane ring having various substituent groups thereon, and hence can be prepared through various synthetic routes adapted for the individual chemical structures.

Method 1

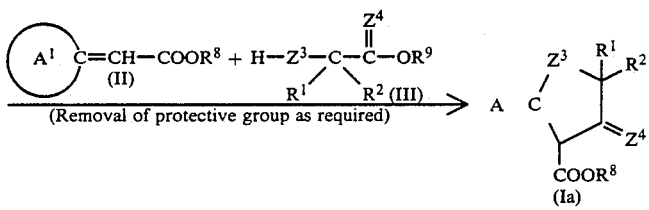

Method 2

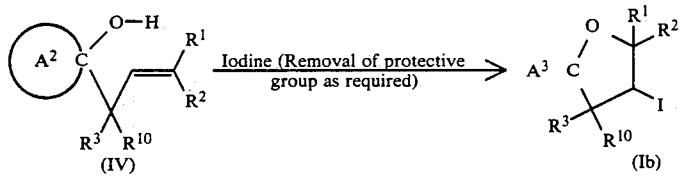

Method 3

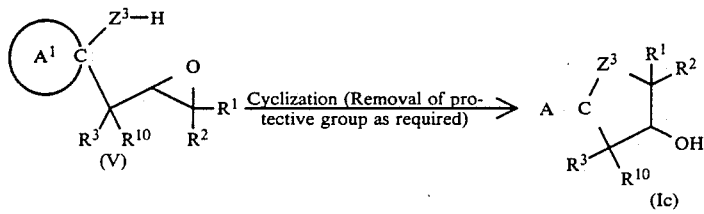

Method 4

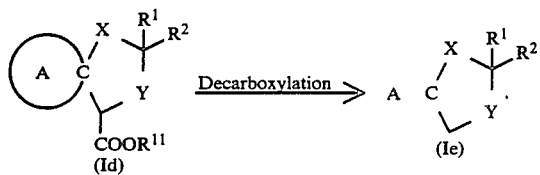
(Id) → (Ie)

Method 5

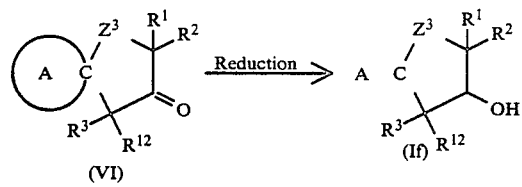
(VI) → (If)

Method 6

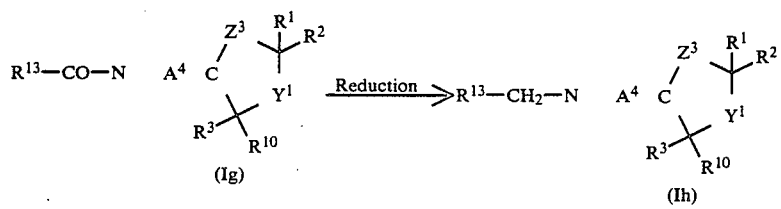
(Ig) → (Ih)

Method 7

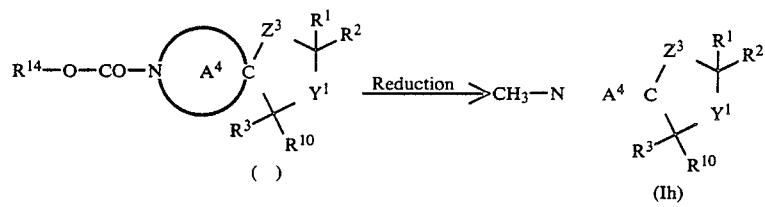
( ) → (Ih)

Method 8

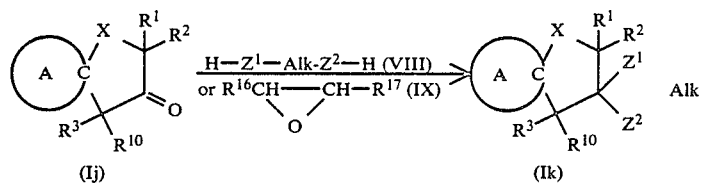
(Ij) → (Ik)

Method 9

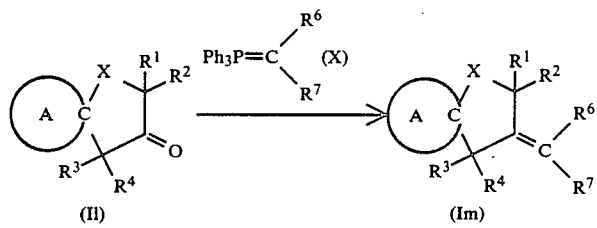
(Il) → (Im)

(wherein ring A, $R^1$, $R^2$, $R^3$, $R^4$, $R^5$, $R^6$, $R^7$, X, Y, $Z^1$, $Z^2$ and Alk are as defined above, ring $A^1$ means a piperidine ring in which the nitrogen atom may optionally be substituted by a lower alkyl, a lower alkanoyl, a lower alkoxycarbonyl or a protective group for amines, and in which the nitrogen atom may be connected to any position carbon (which is not the common carbon atom of the spiro structure) via lower alkylene; ring $A^2$ means a piperidine ring in which the nitrogen atom is substituted by a lower alkanoyl, a lower alkoxycarbonyl or a protective group for amines; and in which the nitrogen atom may be connected to any position carbon (which is not the common carbon atom of the spriro structure) via lower alkylene; ring $A^3$ means a piperidine ring in which the nitrogen atom may optionally be substituted by a lower alkanoyl or a lower alkoxycarbonyl, and in which the nitrogen atom may be connected to any position carbon (which is not the common carbon atom of the spiro structure) via lower alkylene; ring $A^4$ means a piperidine ring as a ring structure in which the nitrogen atom does not bear any sustituent (that is, $A^4$ does not mean

but means

$Y^1$ is a radical represented by

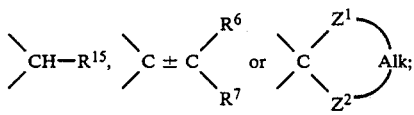

$Z^3$ and $Z^4$ are same or different oxygen atom or sulfur atom; $R^8$ and $R^9$ are same or different lower alkyl; $R^{10}$ is hydrogen atom or a lower alkyl; $R^{11}$ is hydrogen atom or a lower alkyl; $R^{12}$ is hydrogen atom, a lower alkyl, carboxyl or a lower alkoxycarbonyl; $R^{13}$ is hydrogen atom or an alkyl group of 1 to 5 carbon atoms; $R^{14}$ is a lower alkyl; $R^{15}$ is hydroxyl, mercapto, a lower alkoxy or a lower alkylthio; Ph is phenyl; and $R^{16}$ and $R^{17}$ are same or different hydrogen atom or a lower alkyl.)

Detailed below is each of the above preparative methods.

Method 1

There are many cyclization processes for preparing the compounds of this invention. Compounds represented by the general formula (Ia) can be advantageously synthesized by cyclic condensation between an ester of a cycloalkylideneacetic acid (II) and an ester of an hydroxy(or mercapto)-alkyl-(thio)carboxylic acid (III), followed by removal of the protective group as required.

In this method, a compound (II) and an alkali metal salt of a compound (III) are allowed to react, or a compound (II) and a compound (III) are allowed to react in the presence of a base, in which the two reactants are used in equimolar amounts or one of the reactants is used in slight excess. The reaction is preferably carried out in an inert organic solvent under cooling or at room temperature. Suitable solvents are aprotic compounds, such as dimethyl sulfoxide, benzene, toluene, xylene, dichloromethane, tetrahydrofurane, N,N-dimethylformamide, dichloroethane, chloroform and carbon tetrachloride. Of these, dimethyl sulfoxide or tetrahydrofurane, is the most preferred. The alkali metal salt of compound (III) can be obtained by reaction of a compound (III) with a base, such as sodium hydride, preferably under anhydrous conditions. The same type of base may be used in the reaction of a compound (II) and a compound (III) in free form.

Any types of protective groups commonly employed for amino groups may be used in this invention. These include groups of urethane type (e.g., t-butoxycarbonyl), groups of acyl type (e.g., formyl, acetyl and propionyl), and groups of benzyl type (e.g., benzyl, benzhydryl and trityl). Removal of these protective groups may be effected by usual methods; in the presence of an acid or a base for those of urethane type, in the presence of a base for those of acyl type, and by catalytic reduction for those of benzyl type. Hydrochloric acid, trifluoroacetic acid and hydrobromic acid/acetic acid may be mentioned as the acid catalyst used, and sodium hydroxide and potassium hydroxide may be mentioned as the base catalyst.

Compounds (II), as described in Reference Example 3, can be obtained by reaction of an oxo-heterocyclic compound carrying protective group, lower alkyl, lower alkanoyl and lower alkoxycarbonyl with a lower alkyl dialkylphosphonoacetate in an inert solvent (e.g., dimethoxyethane, dioxane and tetrahydrofuran) in the presence of a base under cooling or at room temperature, or by the normal Wittig reaction, followed by removal of the protective group.

Method 2

Spiro compounds of 3-iodo-heterocyclic type represented by the general formula (Ib) can be prepared by iodination of an alkenyl-substituted, heterocyclic alcohol represented by the general formula (IV), followed by removal of the protective group as required.

The reaction is preferably carried out by dissolving a compound (IV) in an inert organic solvent, adding an aqueous alkaline solution of iodine in a more than stoichimetric amount, and holding the resulting mixture under cooling or at room temperature.

Suitable organic solvents are aprotic compounds, such as dichloromethane, dichloroethane, chloroform, carbon tetrachloride, benzene, toluene, zylene and dimethyl sulfoxide, and sodium carbonate, potassium carbonate, sodium bicarbonate, sodium hydroxide and potassium hydroxide may be mentioned as examples of the alkali.

The type of protective groups and methods for removing the same are practically the same as in Method 1.

Compounds (IV) (starting material) are novel compounds, which can be easily obtained, as shown in the reaction formula given below, by the action of a Grignard reagent, prepared from an alkenyl halide and magnesium by usual method, upon an oxo-heterocyclic compound.

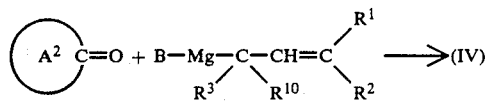

(wherein ring $A^2$, $R^1$, $R^2$, $R^3$ and $R^{10}$ are as defined above; and B is a halogen atom).

Method 3

The compounds of this invention represented by the general formula (Ic) can be synthesized by subjecting an epoxy compound of general formula (V) to cyclization reaction, followed by removal of the protective group as required.

This cyclization is effected by the action of a Lewis acid (such as tin tetrachloride, titanium tetrachloride and boron trifluoride/diethyl ether complex) upon a compound (V) dissolved in an inert organic solvent, followed by addition of a base.

Suitable organic solvents are aprotic compounds, such as dichloromethane, dichloroethane, chloroform, carbon tetrachloride, benzene, toluene, xylene and dimethyl sulfoxide. The base may be any compound that can trap the hydrochloric acid and metal salt formed, illustrative examples being organic bases, such as triethylamine, trimethylamine, pyridine, picoline, lutidine and dimethylaniline; and inorganic bases, such as sodium hydroxide, potassium hydroxide, sodium carbonate and potassium carbonate.

The reaction is preferably carried out under cooling or at room temperature.

The types of protective groups and methods removing the same are practically the same as in Method 1.

Method 4

The compounds of this invention represented by the general formula (Ie) can be synthesized by decarboxylation of a corresponding compound (Id) carrying carboxyl or a lower alkoxycarbonyl as the substituent group at 4-position.

The decarboxylation reaction is effected by heating (preferably heating under reflux) in the presence of an acid. When the substituent group is a lower alkoxycarbonyl, a process may be adopted in which the starting material (Id) is dissolved in an inert organic solvent (e.g., diemthylformamide and dimethyl sulfoxide) and this solution is heated in the presence of an equimolar or more amount of sodium chloride. When the process of Method 1 is followed by the process of this method, the reaction product in the preceding step need not be isolated, but it may be heated in the form of an acidic aqueous solution for direct conversion into compound (Ie).

Method 5

Compounds of this invention can be prepared through reduction, and various reduction procesess may be adopted depending on the type of radical to be reduced.

Method 5 is a process for obtaining compounds (If) carrying hydroxyl as substituent at 3-position by reduction of a corresponding compound in which the 3-position is carbonyl.

The reaction is preferably carried out in an inert solvent (for example, alcohols, such as methanol, ethanol and isopropanol, tetrahydrofuran, and dioxane) at room temperature or at an elevated temperature using a reducing agent that can selectively reduce the carbonyl at 3-position (a boron hydride compound, such as sodium borohydride and sodium cyanoborohydride).

Method 6

N-lower-alkyl compounds represented by the general formula (Ih) can also be synthesized by reduction of a starting material (Ig) carrying a lower alkanoyl as the substituent group at N-position.

The reaction is preferably carried out in an organic solvent (e.g., ether, tetrahydrofuran and dioxane) using, as reducing agent, an aluminum hydride compound (such as lithium aluminum hydride) at room temperature or at an elevated temperature.

Method 7

N-methyl compounds of this invention represented by the general formula (Ii) can be synthesized by reduction of a compound (III) carrying a urethane-type substituent at the N-position.

The reduction is preferably effected in an organic solvent (e.g., tetrahydrofuran, ether and dioxane) using, as reducing agent, aluminum hydride (prepared from lithium aluminum hydride and sulfuric acid) at room temperature or at an elevated temperature, or under cooling.

Method 8

Cyclic ketals represented by the general formula (Ik) can be synthesized by methods commonly employed for the preparation of cyclic ketals. For example, a corresponding carbonyl compound represented by the general formula (Ij) is allowed to react with a compound (VIII), such as a glycol, a hydroxyalkanethiol or an alkanedithiol, or with an epoxy compound (IX), to form a compound (Ik).

The reaction is carried out by dissolving a compound (Ij) and an equimolar or excess amount of a compound (III) in an inert organic solvent (preferably a solvent adapted for azeotropic dehydration, such as benzene, toluene and xylene) and heating the solution under reflux in the presence of an acid catalyst to effect dehydration (preferably using a Dean-Stark azeotropic dehydration apparatus). As the acid catalyst, may be used adipic acid, oxalic acid and pyridine hydrochloride, but the use of ptoluenesulfonic acid is the most preferred. If the reaction is carried out in an inert solvent, such as dichloromethane, dichloroethane, chloroform, carbon tetrachloride, ether, dioxane and tetrahydrofuran, in the presence of a Lewis acid (e.g., boron trifluoride/diethyl ether and tin tetrachloride), the objective product can be obtained without dehydration or heating. When an epoxy compound (IX) is used as a starting material, the reaction is carried out in an inert solvent (e.g., dichloromethane, dichloroethane, chlorform and carbon tetrachloride) in the presence of stannous chloride or boron trifluoride/ether complex at room temperature or at an elevated temperature, or in the presence of tetraethylammonium bromide at 80 to 150° C. in an autoclave.

Method 9

Compounds of general formula (Im) having an alkylidene group at the 3-position can be synthesized by reaction of a corresponding compound (Il) in which the 3-position is carbonyl with an alkyltriphenylphospholane (X).

This reaction is preferably carried out in an inert, aprotic organic solvent (such as dimethyl sulfoxide, dimethylformamide, tetrahydrofuran, ether, dioxane, benzene, toluene and xylene) under cooling or at an elevated temperature using an equimolar or excess amount of compound (X). The compound (X) can be prepared by reaction of a corresponding alkyltriphenylphosphnium halide with an equimolar or excess amount of a base in the same solvent as above under cooling or heating. As the base, may be preferably used sodium hydride or n-butyllithium.

Other Methods

Many other methods may be applied to the preparation of the compounds of this invention.

For example, esters can be synthesized by reaction of a corresponding carboxylic acid or a reactive derivative thereof with a lower alcohol or a reactive derivative thereof (e.g., a lower alkyl halide) in the presence of a condensation agent or a base as required, or by other commonly used esterification techniques. On the contrary, compounds of this invention having free carboxyl group can be derived from a corresponding ester by hydrolysis. Thiocarboxylic acids and esters thereof can be similarly prepared.

Compounds in which the 3-position is thiocarbonyl can also be synthesized (other than by Method 1) by the action of phosphorus pentasulfide or a Lawelsson's reagent (preferably used when no amide nor ester bond is present) upon a compound in which the 3-position is carbonyl.

Compounds carrying a lower alkyl as substituent group at the N-position can be derived from a corresponding free-nitrogen compound by the usual N-alkylation method using a lower alkyl halide or the like, or by the action of a lower alkylaldehyde in the presence of a reducing agent, such as sodium borohydride and sodium cyanoborohydride. Compounds carrying a lower alkanoyl as substituent group at the N-position can be derived from a corresponding free-nitrogen compound by the usual amidation method using a lower alkanoic acid or a reactive derivative thereof in the presence of a base as required.

Compounds of this invention carrying mercapto substituent group at the 3-position can be synthesized by sulfonating a corresponding compound carrying hydroxy substituent group at the 3-position (which may optionally have a protective group, followed by the action of a thiocarboxylic acid (such as thioacetic acid, $CH_3CO-SH$), hydrolysis and removal of the protective group as required; or by forming a corresponding N-alkyl compound according to Method 6 or Method 7.

Compounds carrying a thioether substituent group at the 3-position can be derived from the mercapto compound obtained above or an alkali metal salt thereof by the action of a lower alkyl halide or a lower alkyl sulfonate (preferably p-toluenesulfonate) in the presence of a base as required.

Compounds carrying an ether substituent group at the 3-position can be derived from a corresponding 3-hydroxy compound by the action of a lower alkyl halide (e.g., a lower alkyl iodide) in the presence of a base, followed by removal of the protective group as required; or by forming a corresponding N-alkyl compound according to Method 6 or Method 7.

The compounds of this invention (I) thus prepared are isolated and purified in the free form or as a salt (salts can be obtained by commonly used salt-forming reactions).

Isolation and purification are effected by commonly employed chemical operations, such as liquid/liquid separation, extraction, concentration, crystallization, filtration, recrystallization, and various types of chromatography.

As stated above, the compounds of this invention may be obtained in different isomeric forms (such as geometric isomers, racemic compound, optical isomers and diastereomers), either alone or as a mixture thereof. Geometric isomers can be separated by properly selecting the starting material or by utilizing the difference in physicochemical properties among the isomers. Optical isomers and diastereomers can be separated by properly selecting the starting material, by the general racemic separation techniques (for example, leading to diastereomer salts with an optically active acid, such as tartaric acid, followed by optical resolution), or by techniques commonly used for diastereomer separation (for example, fractional crystallization and chromatography).

When some of the preparative methods described above are to be used in succession, the reaction steps with no explanation about protective groups may also be carried out with protective groups attached.

The Effects of the Invention

The compounds of this invention (I) act directly upon muscarinic acethylcholine receptor and thus have ability to activate cholinergic function in central nervous system.

Activities of choline acetyltransferase, acetylcholine esterase in Alzheimer-type dementia patients (hereinafter, referred to as "ATD") are significantly reduced in some brain regions such as hippocampus, amygdala, cerebral cortex [cf. Davies, P., Maloney, A. J. F., Lancet, ii, 1,043 (1976)]; however, if found no significant change of activities of glutaminic acid decarboxylase, tyrosine, hydroxylase, dopaminebeta-hydroxylase, monoamine oxydase, etc. These findings suggest that functional decrease of cholinergic nervous system was occurred in gloval brain region [cf. Davies, P.; Brain Res. 171, 319 (1979)]. Further, it is suggested that deficit of memory and orientation in the case of ATD or senile dementia have close relation to functional decrease or loss of acetylcholinergic nerve [cf. Whitehouse, P. J. et al, Science 215, 1,237, (1982); Perry, E. K. et al., Brit, Med, J. 2, 1,457 (1978)].

Muscarinic receptors are classified in two kinds of subtype, $M_1$ and $M_2$ [Trends Pharmacol. Scei. Suppl. (1984)]. $M_1$-subtype exist maily in cerebral cortex, hippocampus, corpus striatum and in ganglion of sympthetic nervous.

$M_2$-subtype exist maily in cerebellum and some peripheral tissues such as smooth muscle, cardiac muscle, gland, etc. [Vickroy, T. W. et al., Fred. Proc., 43, 2,785 (1984)]. From the results of animal experiments, it is suggested that the $M_1$-subtype has relation to learning and memory function [cf. Caufield, M. P. et al., J. Pharm. Pharmacol. 35, 131 (1983)] and the $M_2$-subtype has relation to heart inhibition, tremor, etc. [cf. Mutschler, E., Lambrecht, G., Trends Pharmacol. Sci. Suppl., 39 (1983), Palacios, J. M. et al., Eur. J. Pharmacol. 125, 45 (1986)].

Thus, it is believed that muscarinic agonist having $M_1$-receptor-selectivity may improve intelectual deficits such as loss of memory, loss of orientation, in the case of senile dementia.

The compounds of this invention have selective affinity to $M_1$-receptor, and thus are useful for treating diseases caused by central nervous system degeneration (in particular, diseases caused by decrease of acetylcholine function) such as ATD, ATD-type senile dementia, Huntington's chorea, Pick's desease, etc.

The effects of the present compounds were determined by improvement of amnesia, induction of tremor and inhibition of $^3H$-ligand finding to membranes of rat brain. Oxotremorine and Arecoline (typical muscarine receptor agonists) were used as comparison compounds, and the results are shown in Table 1.

(1) Improvement of amnesia caused by scopolamine in rats:

Improving effects of the compounds on amnesia caused by intraperitoneal administration (1 mg/lg) of scopolamine hydrobromide were determined in accordance with a method described in "Jarvik, M. E. et al., Psychol. Resp. 21, 221 (1967)". The test compounds were administered subcutaneously at the same time as the administration of scopolamine hydrobromide.

(2) Induction of tremor in mice:

The compounds were administered subcutaneously in mice. Minimum effective dose for causing tremor was determined.

(3) Affinity for muscarinic receptor:

Tests were done almost in accordance with a method described in "Watson, M. et. al., Life Science 31, 2,019 (1982)" on the affinity of [3H]pirenzepine to $M_1$-receptor of rat cerebral cortex, and a further test was done in accordance with a method of "Yamamura, H. I., Snyder, S. H., Proc. Natul. Acad. Sci., U.S.A., 71(5), 1,725 (1974)" on the affinity of [3H]quinuclifinyl benzylate (QNB) to $M_2$-receptor of rat cerebellum.

TABLE 1

| Compounds | Dose (mg/kg, sc) | | Receptor-affinity $IC_{50}(\mu\text{-M})$ | |
|---|---|---|---|---|
| | The effect of the above (1) | The effect of the above (2) | Pirenzepine-binding | QNB-binding |
| Example | | | | |
| 5 | 0.5 | >30 | 3.32 | 25.1 |
| 15 | 0.03 | >30 | 0.37 | 2.14 |
| 22 | 0.03 | >30 | 0.039 | 0.71 |
| 29 | 0.03 | >30 | 0.049 | 0.64 |
| 33 | 0.03 | >30 | 0.017 | 0.31 |
| 36 | 0.3 | >30 | 1.26 | 8.96 |
| Oxotremorine | 0.2 | 0.2 | 0.068 | 0.0049 |
| Arecoline | 2.5 | 5 | 0.85 | 0.73 |

From the Table I, it is apparent that the compounds of this invention have excellent pharmacological effects.

The formula (I) compounds of this invention or their pharmaceutically acceptable salts may be formulated into ordinary dosage forms such as, for example, tablets, capsules, pills, solutions, etc., and these medicaments can be prepared by conventional methods using usual medical exipients. That is, medical agents containing the compounds of this invention or their salt may be prepared by conventional methods using conventional carriers or excipients. They may for example administered orally as tablet, powder, troche, pills, capsules, granules; parenterally by intravenous or intramuscular or subcutaneous injection; suppositories; or other suitable forms for administration in liquid, fluid, or solid state, for example ointment, adhesive tape, plaster, etc.

The appropriate dose of the present compounds is determined in each case considering factors such as the kind of the compounds, the symptom, age, sex, body weight, administration route, etc., but for an adult about 0.001-10 mg (preferably, 0.01-0.1 mg) per single dose, for injection-administration, is usually administered; and for oral administration, about 0.05-500 mg (preferably, 0.1-10 mg) per single dose is administered usually; the medicaments are administered in one to 3 devided doses per a day.

(EXAMPLES)

The following examples will further illustrate the invention. Some of the starting materials used for the synthesis of the compounds of this invention are novel compounds. Preparative methods for these novel compounds are described in Reference Examples.

EXAMPLE 1

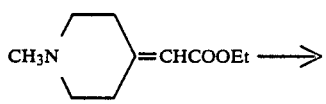

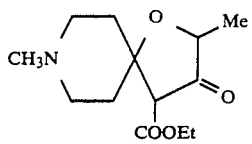

To a three-necked flask fitted with a thermometer, a dropping funnel and a calcium chloride tube, was put 4 g of 60% oily sodium hydride, and the oil component was washed off by treatment with n-hexane. Anhydrous ether (150 ml) was added to the residue, the mixture was stirred well, and 50 ml of an ethereal solution containing 11.8 g ethyl lactate was then added at 5 to 10° C. Evolution of hydrogen gas ceased after stirring at room temperature for about three hours. The ether was distilled off under reduced pressure, 80 ml dimethyl sulfoxide was added to the residue, the resulting solution was cooled to about 15° C., and 18.3 g ethyl 1-methyl-4-piperidylideneacetate was added. After stirring at room temperature for about 20 hours, the reaction mixture was poured into 200 ml ice water, concentrated hydrochloric acid was added dropwise until the pH fell to about 4, and sodium bicarbonate was then added to make the solution weakly alkaline. To this aqueous solution, was added sodium chloride until saturation, the saturated solution thus obtained was extracted thrice with 300 ml chloroform, and the combined extract was washed with saturated aqueous solution of sodium chloride and dried over anhydrous magnesium sulfate. Distilling off the chloroform under reduced pressure from the dried solution left 16 g of an oily mixture containing much dimethyl sulfoxide. It was purified by silica gel column chromatography using, as eluent, a mixed solvent of chloroform/methanol/conc. ammonia (10:1:0.1 by volume), giving 2.9 g of ethyl 2,8-dimethyl-3-oxo-1-oxa-8-azaspiro[4.5]decane-4-carboxylate as solid.

Physicochemical properties

Mass spectrum (m/z): 255, 181, 136

IR absorption spectrum (KBr) cm$^{-1}$: 3,500(broad), 1,672, 1,552

NMR spectrum (CDCl$_3$; internal standard: TMS), δppm:

1.16–1.48 (m, 6H, —OCH$_2$CH$_2$CH$_3$, C—CH$_3$),

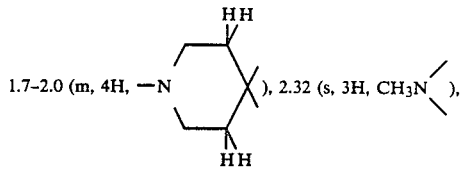

2.3-2.8 (m, 4H, —N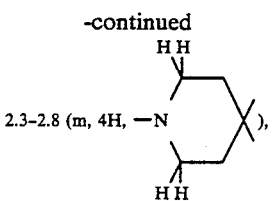), 4.0-4.2 (m, 3H, —OC$\underline{H}_2$CH$_3$, 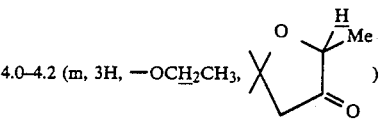)

EXAMPLE 2

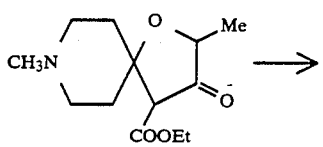 →

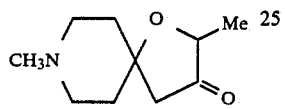

Ethyl 2,8-dimethyl-3-oxo-1-oxa-8-azaspiro[4,5]decane-4-carboxylate (3.08 g) was dissolved in 50 ml of 1N-HCl, and the solution was heated under reflux for eight hours. The reaction mixture was allowed to cool to room temperature, then cooled in an ice-water bath, and basified by addition of 20% aqueous solution of caustic soda. This alkaline solution was extracted thrice with about 80 ml of chloroform, and the combined extract was washed with saturated aqueous solution of sodium chloride and dried over anhydrous magnesium sulfate. Distilling off the solvent under reduced pressure from the dried solution left 2 g of yellow residue, which was purified by silica gel column chromatography by using, as eluent, a mixed solvent of chloroform/methanol (20:1 by volume), giving 1.8 g of 2,8-dimethyl-1-oxa-8-azaspiro[4,5]decan-3-one as oil. It was dissolved in ether, and ethanolic hydrogen chloride was added, thus giving its hydrochloride as crystals.

Physicochemical properties

Melting point: 179–181° C. (dec.)
Elemental analysis (C$_{10}$H$_{18}$NO$_2$Cl):

|  | C(%) | H(%) | N(%) | Cl(%) |
|---|---|---|---|---|
| Calcd. | 54.67 | 8.26 | 6.38 | 16.14 |
| Found | 54.40 | 8.27 | 6.31 | 16.35 |

Mass spectrum (m/z): 183, 110
IR absorption spectrum (KBr) cm$^{-1}$: 3,500(broad), 2,400–2,700, 1,754
NMR spectrum (CDCl$_3$; internal standard: TMS), δppm:

1.30 (d, 3H, J=7.2Hz, C—CH$_3$), 1.8–2.5 (m, 4H,

—N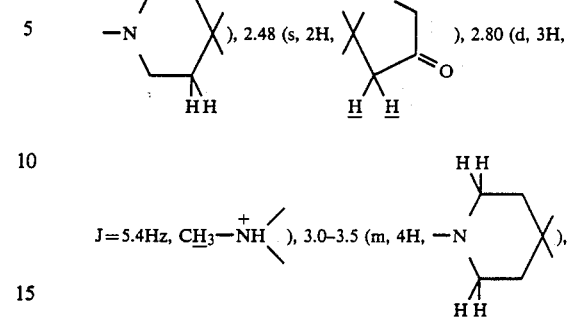), 2.48 (s, 2H, ), 2.80 (d, 3H,

J=5.4Hz, CH$_3$—$\overset{+}{N}$H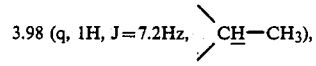), 3.0–3.5 (m, 4H, —N), 3.98 (q, 1H, J=7.2Hz, $\diagdown$C$\underline{H}$—CH$_3$),

EXAMPLE 3

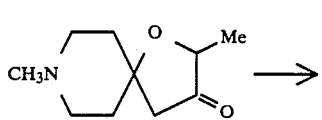 →

Me

CH$_3$N ⟨structure⟩ OH

To a solution of 2,8-dimethyl-1-oxa-8-azaspiro[4.5]-decan-3-one (200 mg) in 7 ml ethanol, was added 25 mg sodium borohydride at room temperature, and the mixture was stirred at room temperature for two hours. The reaction mixture was cooled in an ice-water bath, acidified by addition of 6N-HCl (to about pH 4), and stirred for about 20 minutes with the ice-water bath removed. Ethanol was distilled off under reduced pressure, and the residue was purified by silica gel column chromatography by using, as eluent, a mixed solvent of chloroform/methanol/conc. ammonia (5:1:0.1 by volume), giving 200 mg of 3-hydroxy-2,8-dimethyl-1-oxa-8-azaspiro[4.5]decane as oil. It was dissolved in ether, and ethanolic hydrogen chloride was added to this solution, thus giving its hydrochloride as white crystals.

Physicochemical properties

Melting point: 174–178° C.
Elemental analysis (C$_{10}$H$_{20}$NO$_2$Cl):

|  | C(%) | H(%) | N(%) | Cl(%) |
|---|---|---|---|---|
| Calcd. | 54.17 | 9.09 | 6.32 | 15.99 |
| Found | 53.90 | 9.22 | 6.27 | 16.05 |

Mass spectrum (m/z): 185, 168, 110
NMR spectrum (CDCl$_3$; internal standard: TMS), δppm:

1.25 (m, 3H, C—CH$_3$), 1.6–2.6 (m, 6H,

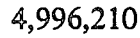

-continued

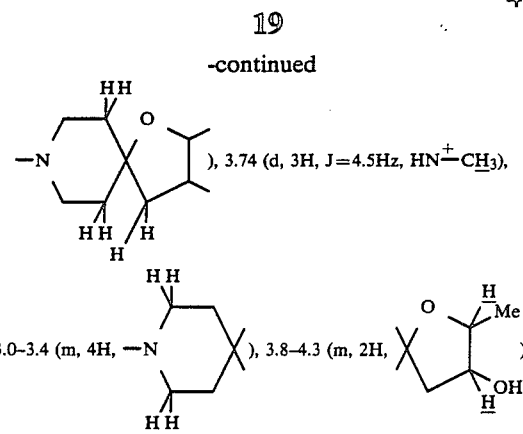

), 3.74 (d, 3H, J=4.5Hz, HN$^{\pm}$C$\underline{H}_3$), 3.0–3.4 (m, 4H, —N\<group\>), 3.8–4.3 (m, 2H, \<group\>)

EXAMPLE 4

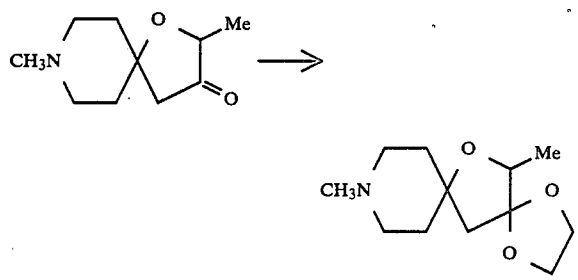

A mixture of 730 mg 2,8-dimethyl-1-oxa-8-azaspiro[4.5]-decan-3-one, 2.25 ml ethylene glycol, 836 mg p-toluenesulfonic acid monohydrate and 30 ml toluene was heated under reflux for 3 hours with a Dean-Strak azeotropic dehydration apparatus, and the reaction mixture was poured into 30 ml of an aqueous solution containing 1.26 g sodium becarbonate. The resulting mixture was extracted with chloroform. The extract was dried over anhdyrous magnesium sulfate, and concentrated under reduced pressure. The residue was purified by silica gel column chromatography on silica gel eluted with a mixed solvent of chloroform/methanol/conc. ammonia (20:1:0.1 by volume) to give 640 mg of 10,14-dimethyl-1,4 13-trioxa-10-azasprio[4.1.5.2-]tetradecane as oil. It was dissolved in isopropanol, and a solution of maleic acid in isopropanol was added to convert it to the corresponding maleate, which was recrystallized from dichloromethane/ether.

Physicochemical properties

Melting point: 106–108° C.
Elemental analysis ($C_{16}H_{25}NO_7$):

|  | C(%) | H(%) | N(%) |
|---|---|---|---|
| Calcd. | 55.97 | 7.34 | 4.08 |
| Found | 55.81 | 7.14 | 4.04 |

Mass Spectrum (m/z): 227, 183, 110

IR absorption spectrum (KBr) cm$^{-1}$: 3,500, 2,960, 2,710, 1,590

NMR spectrum (CDCl$_3$; internal standard: TMS), δppm:

1.15 (d, 3H, J=6.3Hz, C—CH$_3$), 1.9–2.1 (m, 6H,

-continued

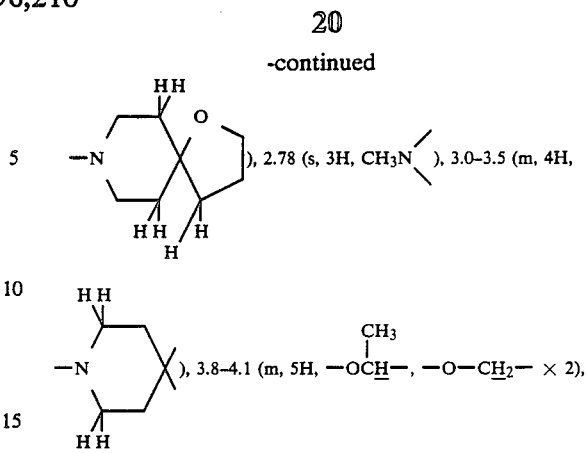

), 2.78 (s, 3H, CH$_3$N\<), 3.0–3.5 (m, 4H,

), 3.8–4.1 (m, 5H, —OC$\underline{H}$—, —O—C$\underline{H}_2$— × 2),

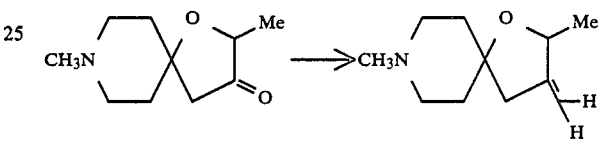

6.28 (2, 2H, $\underline{H}$C=C × 2)

EXAMPLE 5

60% oily sodium hydride (272 mg), placed in a flask, was treated with n-hexane in an argon gas atmosphere to wash off the oil component, and the remaining hexane was distilled off under reduced pressure. Dimethyl sulfoxide (8 ml) was added to the residue, the mixture was heated at 60 to 70° C. for about one hour, the faint-green solution thus obtained was ice-cooled, and 2.43 g methyltriphenylphosphonium bromide was added. Heating the mixture at about 40° C. put the solid into solution, giving a yellowish-red solution. It was cooled to about 30° C., 590 mg 2,8-dimethyl-1-oxa-8-azaspiro[4,5]decan-3-one was added, and the mixture was stirred at room temperature for about two hours. It was then poured into 50 ml ice water, the resulting mixture was extracted with chloroform, and the extract was washed with saturated aqueous solution of sodium chloride and dried over anhydrous magnesium sulfate. After distilling off the solvent under reduced pressure from the dried solution, the residue was purified by silica gel column chromatography by using, as eluent, a mixed solvent of chloroform/methanol (10:1 by volume), giving 320 mg of 2,8-dimethyl-3-methylene-1-oxa-8-azaspiro[4.5]decane as oil. It was dissolved in ether, and ethanolic hydrogen chloride was added to the solution, giving the corresponding hydrochloride as crystals.

Physicochemical properties

Melting point: 190–191° C.
Elemental analysis ($C_{11}H_{20}NOCl.0.3H_2O$):

|  | C(%) | H(%) | N(%) |
|---|---|---|---|
| Calcd. | 59.21 | 9.31 | 6.27 |
| Found | 59.10 | 9.07 | 6.29 |

Mass spectrum (m/z): 181, 166, 96

NMR spectrum (CDCl$_3$; internal standard: TMS), δppm:

1.30 (d, 3H, J=5.4Hz, C—CH3), 1.6–2.4 (m, 4H,

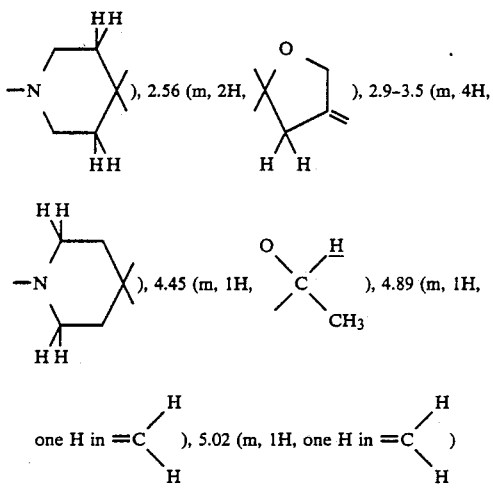

), 2.56 (m, 2H, ), 2.9–3.5 (m, 4H, ), 4.45 (m, 1H, ), 4.89 (m, 1H, one H in =C ), 5.02 (m, 1H, one H in =C )

In similar way, fumarate (mp. 104–106° C.) was obtained.

EXAMPLE 6

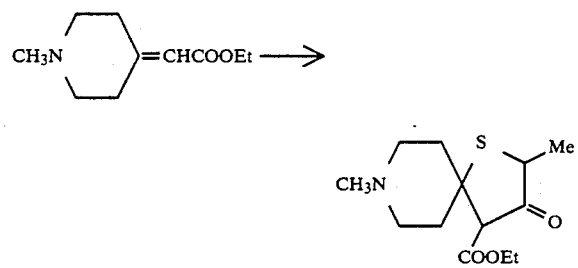

To a three-necked flask fitted with a thermometer, a dropping funnel and a calcium chloride tube, was put 1.04 g of 60% oily sodium hydride, and the oil component was washed off by treatment with n-hexane. Anhydrous ether (35 ml) was added to the residue, the mixture was stirred well, and 15 ml of an ethereal solution containing 3.2 g ethyl thiolactate was then added at 5 to 10° C., and the mixture was stirred at room temperature for about 30 minutes. The solvents were distilled off under reduced pressure, 20 ml dimethyl sulfoxide was added to the residue, the resulting solution was cooled to about 15° C., and 4.76 g ethyl 1-methyl-4-piperidylideneacetate was added. After stirring at room temperature for about 20 hours, the reaction mixture was poured into 100 ml ice water, concentrated hydrochloric acid was added until the pH fell to about 4, and sodium bicarbonate was then added to make the solution weakly alkaine (pH: about 8). This aqueous solution was extracted thrice with 150 ml chloroform, and the combined extract was washed with saturated aqueous solution of sodium chloride and dried over anhydrous magnesium sulfate. Distilling off the chloroform under reduced pressure from the dried solution left 7.84 g of orange-red oil, which was purified by silica gel column chromatography using, as eluent, a mixed solvent of chloroform/methanol/conc. ammonia (30:1:0.1 by volume), giving 1.89 g of ethyl 2,8-dimethyl-3-oxo-1-thia-8-azaspiro [4.5]decane-4-carboxylate as solid. It was dissolved in ether, and ethanolic hydrogen chloride was added to the solution, thus giving its hydrochloride.

Physicochemical properties

Melting point: 161–164° C.
Elemental analysis ($C_{13}H_{22}NO_3SCl.0.8H_2O$):

|  | C(%) | H(%) | N(%) |
|---|---|---|---|
| Calcd. | 48.45 | 7.38 | 4.35 |
| Found | 48.50 | 7.01 | 4.32 |

Mass spectrum (m/z): 271, 238, 225, 197

IR absorption spectrum (KBr) cm$^{-1}$: 3,540, 3,470, 1,660, 1,620

NMR spectrum (CDCl3; internal standard: TMS), δppm:

1.50 (t, 3H, J=7.2Hz, —OCH2C$\underline{H}$3), 1.54 (d, 3H, J=7.2Hz,

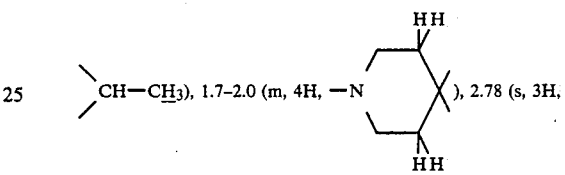

$\underset{/}{\supset}$CH—C$\underline{H}$3), 1.7–2.0 (m, 4H, —N ), 2.78 (s, 3H,

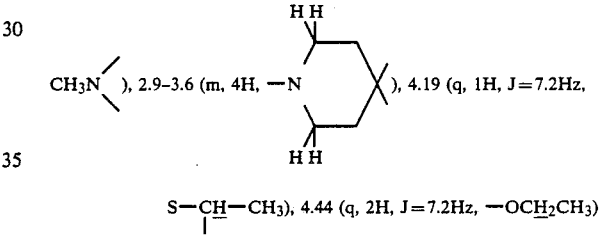

CH3N ), 2.9–3.6 (m, 4H, —N ), 4.19 (q, 1H, J=7.2Hz,

S—C$\underline{H}$—CH3), 4.44 (q, 2H, J=7.2Hz, —OC$\underline{H}$2CH3)

EXAMPLE 7

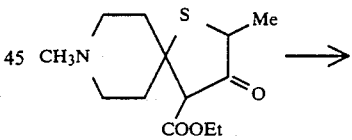

2,8-Dimethyl-1-thia-8-azaspiro[4.5]decan-3-one was prepared (oil) and then converted to its hydrochloride in the same way as in Example 2.

Physicochemical properties

Melting point: 210–213° C.
Elemental analysis ($C_{10}H_{18}NOSCl.0.5H_2O$):

|  | C(%) | H(%) | N(%) |
|---|---|---|---|
| Calcd. | 49.07 | 7.82 | 5.72 |
| Found | 49.15 | 7.63 | 5.77 |

Mass spectrum (m/z): 199, 166, 110

IR absorption spectrum (KBr) cm⁻¹: 3,500, 2,950, 2,700, 17,536

NMR spectrum (CDCl₃; internal standard: TMS), δppm:

1.44 (d, 3H, J=7.2Hz, C—CH₃), 1.9–2.8 (m, 4H,

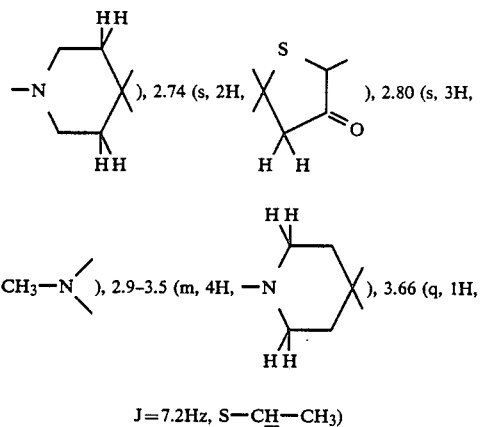

J=7.2Hz, S—CH—CH₃)

EXAMPLE 8

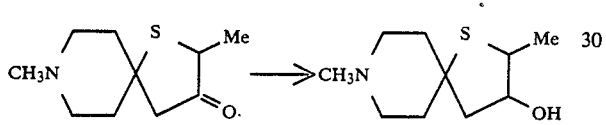

3-Hydroxy-2,8-dimethyl-1-thia-8-azaspiro[4.5]decane was prepared (oil) and then converted to its hydrochloride in the same way as in Example 3.

Physicochemical properties

Melting point: 225–229° C.

Mass spectrum (m/z): 201, 168, 110

IR absorption spectrum (KBr) cm⁻¹: 3,400, 2,970 2,930, 2,700

NMR spectrum (CDCl₃; internal standard: TMS), δppm:

1.32 (d, 3H, J=7.2Hz, C—CH₃), 1.8–2.7 (m, 6H,

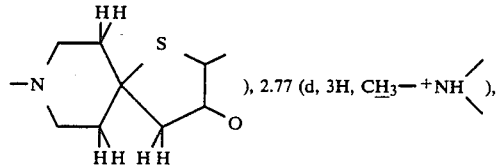

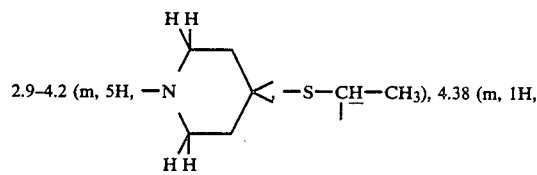

—CH—OH)

EXAMPLE 9

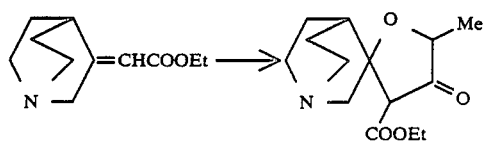

Ethyl 5'-methyl-4'-oxospiro[1-azabicyclo[2.2.2]octane-3,2'-oxolane]-3'-carboxylate was prepared in much the same manner as in Example 1, except that ethyl 3-quinuclidylideneacetate was used in place of 1-methyl-4-piperidylideneacetate.

Physicochemical properties

Mass spectrum (m/z): 268, 267, 221, 194, 166

IR absorption spectrum (KBr) cm⁻¹: 3,480, 2,990–2,890, 1,745, 1,675

NMR spectrum (CDCl₃; internal standard: TMS), δppm:

1.30 (t, 3H, J=7.2Hz, —OCH₂CH₃), 1.43 (d, 3H, J=6.3Hz,

—O—CH—CH₃), 1.5–2.2 (m, 5H, 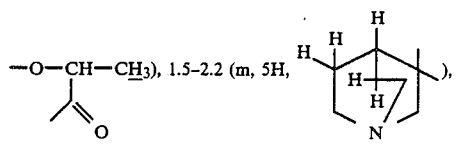), 2.6–3.05 (m, 6H, 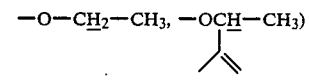 ×3), 4.04–4.32 (m, 3H,

—O—CH₂—CH₃, —OCH—CH₃)

EXAMPLE 10

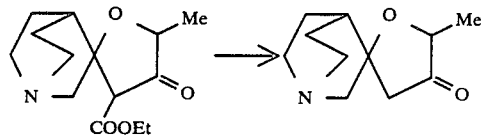

5'-methyl-spiro[1-azabicyclo[2.2.2]octane-3,2'-oxolan]-4'-one was prepared and then converted to its hydrochloride in much the same way as in Example 2.

Physicochemical properties

Melting point: 188–190° C. (dec.)

Elemental analysis (C₁₁H₁₈NO₂Cl):

|  | C(%) | H(%) | N(%) | Cl(%) |
|---|---|---|---|---|
| Calcd. | 57.02 | 7.83 | 6.04 | 15.30 |
| Found | 56.72 | 7.76 | 5.95 | 15.28 |

Mass spectrum (m/z): 195, 138, 96

NMR spectrum (CDCl₃; internal standard: TMS), δppm:

1.33 (m, 3H, C—CH₃), 1.65–2.60 (m, 5H,

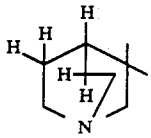), 2.40–3.0 (m, 2H, —CH₂—CO—), 3.2–3.7 (m, 6H, N—CH₂ × 3), 3.85–4.25 (m, 1H, O—C$\underline{H}$—CH₃)

EXAMPLE 11

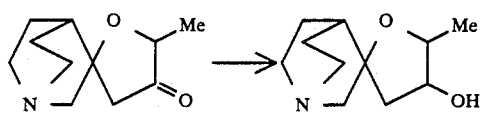

4'-Hydroxy-5'-methyl spiro[1-azabicyclo[2.2.2]octane-3,2'-oxolane] was prepared and then converted to its hydrochloride in much the same way as in Example 3.

Physicochemical properties

Melting point: 162–166° C.
Elemental analysis (C₁₁H₂₀NO₂Cl.0.2H₂O):

|  | C(%) | H(%) | N(%) |
|---|---|---|---|
| Calcd. | 55.66 | 8.62 | 5.90 |
| Found | 55.77 | 8.58 | 5.93 |

Mass spectrum (m/z): 197, 180, 139
NMR spectrum (CDCl₃; internal standard: TMS), δppm:

1.1–1.3 (m, 3H, C—CH₃), 1.5–2.6 (m, 7H,

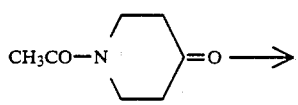), 3.5–3.6 (m, 6H, $\diagdown$N—CH₂— × 3), 3.8–4.35 (m, 2H, —O—C$\underline{H}$—C$\underline{H}$—) with CH₃ OH substituents

REFERENCE EXAMPLE 1

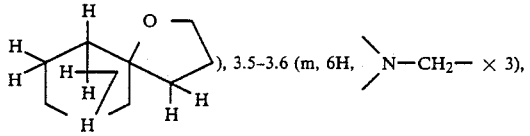

To a solution of 1.94 g 1-acetyl-4-piperidone in a mixture of ether (80 ml) and tetrahydrofuran (40 ml), was added dropwise at 10° C. or lower 275 ml of a 0.5M Grignard reagent prepared by the usual way from crotyl chloride and magnesium, and the resulting mixture was stirred overnight at room temperature. To the ice-cooled reaction mixture, was slowly added 100 ml of saturated aqueous solution of sodium chloride, and the layers were separated. The aqueous layer was extracted with chloroform, the two organic solutions were each concentrated, and the combined concentrate was subjected to silica gel column chromatography using, as eluent, a mixed solvent of ethyl acetate/n-hexane (1:1 by volume) containing 3% methanol, giving 16.9 g of 1-acetyl-4-hydroxy-4-(1-methyl-2-propenyl)piperidine as oil.

NMR spectrum (CDCl₃; internal standard: TMS), δppm:

1.04 (d, 3H, $\diagdown$CH—C$\underline{H}$₃), 2.10 (s, 3$\underline{H}$, CH₃CO—), 2.0–2.3 (m, 1H, $\diagdown$C—$\underline{H}$), 5.0–5.24 (m, 2H, —CH=C$\diagup\underline{H}\diagdown\underline{H}$),
with CH₃

5.6–6.0 (m, 1H, —CH=CH₂)
                        |
                        $\underline{H}$ IR absorption spectrum (neat) cm⁻¹: 3,436, 2,988, 1,622, 1,278, 1,250

Mass spectrum (m/z): 197 (M+), 180, 154, 142

EXAMPLE 12

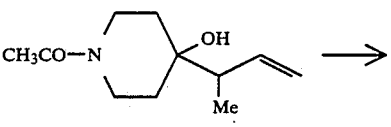

→

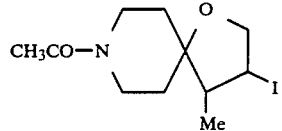

A solution of 1.78 g 1-acetyl-4-hydroxy-4-(1-methyl-2-propenyl)piperidine in 60 ml dichloromethane was cooled in ice, 24 ml water was added, 1.51 g sodium bicarbonate and 3.45 g iodine were then added with stirring, and the mixture was stirred under ice cooling for four hours. The organic layer was collected, the aqueous layer was extracted thrice with chloroform, and all the organic solutions were combined and dried. After distilling off the solvent from the dried solution, the residue was subjected to silica gel column chromatography using, as eluent, a mixed solvent of ethyl acetate/n-hexane (1:1 by volume) containing 3% methanol, giving a diastereoisomeric mixture of 8-acetyl-3-iodo-4-methyl-1-oxa-8-azaspiro[4.5]decane (1.55 g).

Melting point: 135–137° C.
Elemental analysis (C₁₁H₁₈NO₂I):

|  | C(%) | H(%) | N(%) | I(%) |
|---|---|---|---|---|
| Calcd. | 40.88 | 5.61 | 4.34 | 39.27 |
| Found | 40.79 | 5.50 | 4.22 | 39.46 |

NMR spectrum (CDCl₃; internal standard: TMS), δppm:

1.06 (d, 3H, J=5.4Hz, CH—C$\underline{H}_3$), 1.3–2.0 (m, 5H,

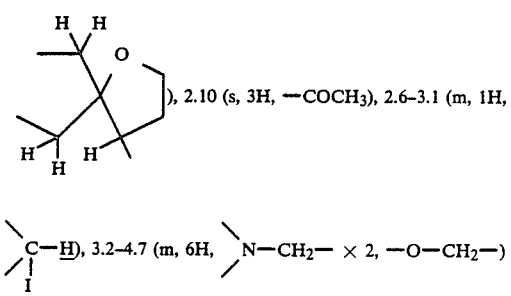

), 2.10 (s, 3H, —COCH$_3$), 2.6–3.1 (m, 1H, $\overset{\diagdown}{\underset{\diagup}{\overset{|}{C}}}$—$\underline{H}$), 3.2–4.7 (m, 6H, $\overset{\diagdown}{\underset{\diagup}{N}}$—CH$_2$— × 2, —O—CH$_2$—)

IR absorption spectrum (KBr) cm$^{-1}$: 1,642, 1,456, 1,428, 1,028

Mass spectrum (m/z): FAB-MS 324

REFERENCE EXAMPLE 2

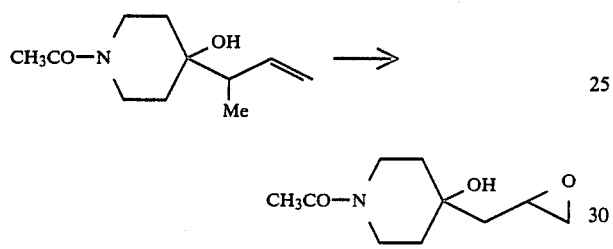

To a solution of 4.76 g 1-acetyl-4-hydroxy-4-(1-methyl-2-propenyl)piperidine in 50 ml dichloromethane, was added 60 g m-chloro-perbenzoic acid, and the mixture was stirred at room temperature for three days. The insoluble matters were filtered off, the filtrate was washed five times with saturated aqueous solution of sodium bicarbonate, and the aqueous washings were combined and extracted with chloroform. All the organic solutions were combined and dried, and the solvent was distilled off from the dried solution. The residue was subjected to column chromatography on silica gel (300 ml) using pure chloroform and chloroform containing 2% methanol as eluents to separate two types of diastereomers of the objective compound. As a result, were isolated 1.62 g of diastereomer (A) (isomer of lower polarity as measured by TLC), 1.66 g of diastereomer (B) (isomer of higher polarity) and 0.14 g of a mixture of both isomers (each as amorphous powder).

Physicochemical properties of
1-acetyl-4-hydroxy-4-[1-2-oxyranyl)ethyl]piperidine
(A)

NMR spectrum (CDCl$_3$; internal standard: TMS), δppm:

1.0 (d, 3H, CH—C$\underline{H}_3$), 1.24 (m, 1H, CH$_3\overset{|}{C}$—$\underline{H}$), 1.7 (m, 4H, 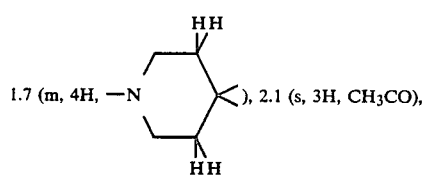), 2.1 (s, 3H, CH$_3$CO), 2,48 (m, 1H, 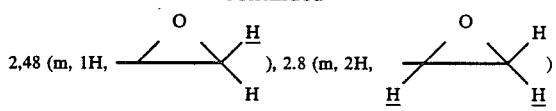), 2.8 (m, 2H, )

Mass spectrum (m/z): 213 (M+), 195, 170, 142, 124

Physicochemical properties of
1-acetyl-4-hydroxy-4-[1-(2-oxyranyl)ethyl]piperidine
(B)

NMR spectrum (CDCl$_3$; internal standard: TMS), δppm:

1.02 (d, 3H, CH—C$\underline{H}_3$), 1.3 (m, 1H, CH$_3$C—$\underline{H}$), 1.66 (m, 4H, 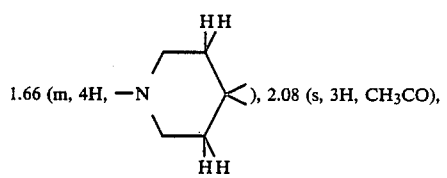), 2.08 (s, 3H, CH$_3$CO), 2.3–3.2 (m, 5H, 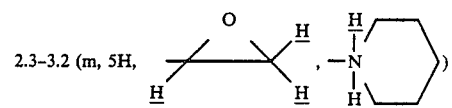)

Mass spectrum (m/z): 213 (M+), 170, 142, 124

EXAMPLE 13

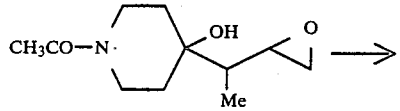

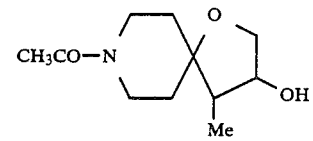

A solution of 1.2 g 1-acetyl-4-hydroxy-4-[1-(2-oxyranyl)ethyl]piperidine (B) in 80 ml dichloromethane was cooled to −40° C., 1.77 g tin tetrachloride was added, and the mixture was stirred at room temperature for two days. The reaction mixture was cooled in ice, 2 ml triethylamine was added, the mixture was concentrated under reduced pressure, and the residue was subjected to silica gel column chromatography using, as eluent, chloroform containing 1 to 5% methanol, giving 0.83 g of 8-acetyl-3-hydroxy-4-methyl-1-oxa-8-azaspiro[4.5]decane (B) as amorphous powder.

NMR spectrum (CDCl$_3$; internal standard: TMS), δppm:

1.0(d, 3H, CH—C$\underline{H}_3$), 1.3–2.0 (5H, —N 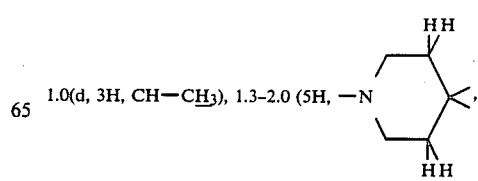,

-continued

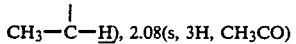, 2.08(s, 3H, CH₃CO)

Mass spectrum (m/z): 213 (M+), 195, 182, 170, 124

Diastereomer (A) obtained in Reference Example 2 was also treated in much the same manner as above, affording 8-acetyl-3-hydroxy-4-methyl-1-oxa-8-azaspiro[4.5]decane (A).

NMR spectrum (CDCl₃; internal standard: TMS), δppm:

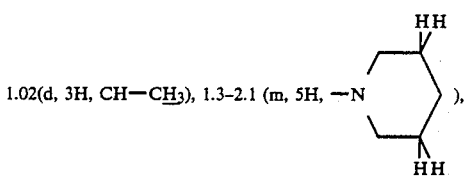

CH₃—C—H̲), 2.20 (s, 3H, CH₃CO)

Mass spectrum (m/z): 213 (M+), 195, 182, 170, 124

EXAMPLE 14

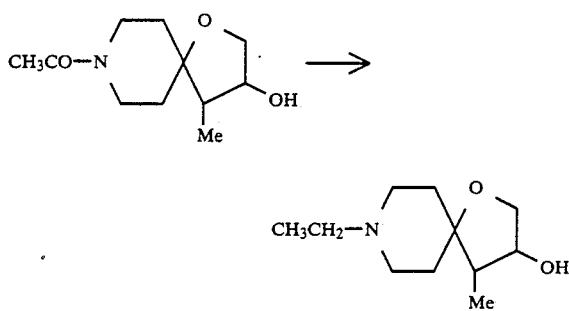

A solution of 0.83 g 8-acetyl-3-hydroxy-4-methyl-1-oxa8-azaspiro [4.5]decane (B) in 20 ml anhydrous tetrahydrofuran was added dropwise to a mixture of 1.01 g lithium aluminum hydride and 25 ml tetrahydrofuran, and the resulting mixture was heated under reflux for three hours and then cooled in ice. Water (1.1 ml) and 10% caustic soda solution (1.1 ml) were slowly added in that order, the reaction mixture was filtered through Celite, and the insoluble matters were thoroughly washed with tetrahydrofuran and ethyl acetate. The washings were joined to the filtrate, the combined solution was concentrated, and the residue was subjected to silica gel column chromatography using, as eluent, a mixed solvent of chloroform/methanol/conc. ammonia (40:10:1), giving 8-ethyl-3-hydroxy-4-methyl-1-oxa-8-azaspiro[4.5]-decane (B) as oil. It was converted to its hydrochloride by treatment with methanolic hydrogen chloride. Yield: 0.4 g, m.p.: 150–155° C.

NMR spectrum (CDCl₃; internal standard: TMS), δppm:

1.02(d, 3H, —CH—CH̲₃), (m, 4H, —NCH₂CH̲₃,

-continued

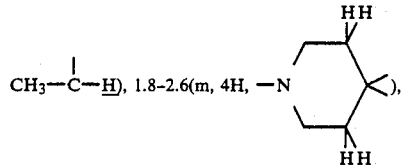

Mass spectrum (m/z): 200 (M+1), 184, 170, 138, 110, 84

IR absorption spectrum (KBr) cm⁻¹: 3,388, 2,948, 2,688 1,418, 1,034, 908

Diastereomer (A) obtained in Example 13 was also treated in much the same manner as above, affording 8-ethyl-3-hydroxy-4-methyl-1-oxa-8-azaspiro[4.5]decane (A). The physicochemical properties of its hydrochloride are as follows:

Melting point: 200–204° C.

Elemental analysis (C₁₁H₂₂NO₂Cl):

|  | C(%) | H(%) | N(%) |
|---|---|---|---|
| Calcd. | 56.04 | 9.41 | 5.94 |
| Found | 55.75 | 9.28 | 5.89 |

NMR spectrum (CDCl₃; internal standard: TMS), δppm:

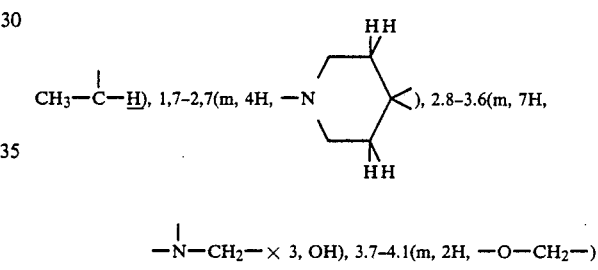

—N—CH₂— × 3, OH), 3.7–4.1(m, 2H, —O—CH₂—)

Mass spectrum (m/z): 199 (M+), 184, 172, 138, 124, 110, 84

IR absorption spectrum (KBr) cm⁻¹: 3,364, 2,948, 2,672, 1,428, 1,062, 1,050

EXAMPLE 15

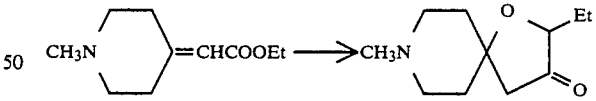

To a three-necked flask fitted with a thermometer, a dropping funnel and a calcium chloride tube, was put 2 g of 60% oily sodium hydride, and the oil component was washed off by treatment with n-hexane. Anhydrous ether (75 ml) was added to the residue, the mixture was stirred well, and 25 ml of an ethereal solution containing 6.6 g ethyl α-hydroxy-n-butyrate was then added at 5 to 10° C. Evolution of hydrogen gas ceased after stirring at room temperature for about three hours. The ether was distilled off under reduced pressure, 40 ml dimethyl sulfoxide was added to the residue, the resulting solution was cooled to about 15° C., and 9.15 g ethyl 1-methyl-4-piperidylideneacetate was added. After stirring at room temperature for about 15 hours, the reaction mixture was poured into 100 ml ice water, concentrated hydrochloric acid was added until the pH fell to about 2, and 4 ml of concentrated hdyrochloric acid was further added. The resulting mixture was heated under reflux for about six hours, and 20% aqueous solution of caustic soda was then added under ice cooling to make the solution alkaline. This alkaline solution was extracted once with 150 ml chloroform and then twice with 100 ml chloroform, and the combined extract was washed with an aqueous solution of sodium chloride and dried over anhydrous magnesium sulfate. Distilling off the chloroform under reduced pressure from the dried solution left 4.96 g of a reddish-brown oily substance. It was purified by silica gel column chromatography using, as eluent, a mixed solvent of chloroform/methanol (30:1 by volume), giving 1.38 g of 2-ethyl-8-methyl-1-oxa-8-azaspiro[4.5]decan-3-one as oil. It was dissolved in ether, and after adding HCl-EtOH, its HCl salt, obtained.

Physicochemical properties

Mass spectrum (m/z): 197, 168, 110

IR absorption spectrum (KBr) cm$^{-1}$: 3,476 (broad), 2,980, 2,728, 1,756

NMR spectrum (CDCl$_3$; internal standard: TMS), δppm:

0.96(t, 3H, J = 7.2 Hz, —OCH$_2$C$\underline{H}$$_3$), 2.45(m, 2H,

—C$\underline{H}$$_2$—CO—), 2.83(s, 3N, —N$\overset{+}{\underline{H}}$—CH$_3$), 1.5–2.8(m, 6H, ), 3.0–3.6(m, 4H, —N⟨⟩, 3.90(m, 1H, —O—C$\underline{H}$(Et)—CO—)

In similar way, fumarate (mp. 77–90° C.), maleate (mp. 126–8° C.) & oxalate (mp. 160–2° C.) were obtained.

EXAMPLE 16

2,8-Dimethyl-3-methylene-1-thia-8-azaspiro[4.5]decane was prepared from 2,8-dimethyl-1-thia-8-azaspiro[4.5] decan-3-one in much the same manner as in Example 5, which was converted to hydrochloride by treating its ethanolic solution with ethanolic hydrogen chloride.

Melting point: 197–200° C.

Mass spectrum (m/z): 197, 164, 96

IR absorption spectrum (KBr) cm$^{-1}$: 3,480 (broad), 2,948, 2,484, 1,660, 1,482

NMR spectrum (CDCl$_3$; internal standard: TMS), δppm:

1.42(d, 3H, J = 7 Hz, ⟩CH—C$\underline{H}$$_3$), 1.8–2.0(m, 2H,

), 2.40–3.16(m, 2H, —N⟨⟩, 2.76(d, 3H, J = 6Hz, CH$_3$—N$\overset{+}{\underline{H}}$ ), 3.4–3.6(m, 2H, ), 4.0 (m, 1H, ⟩C$\underline{H}$—CH$_3$), 4.94(m, 1H, one H in ⟩=C⟨H/H ), 5.0(m, 1H, one H in ⟩C=C⟨H/H )

EXAMPLE 17

3-Ethylidene-2,8-dimethyl-1-oxa-8-azaspiro[4.5]decane was prepared in the same manner as in Example 5 by using ethyltriphenylphosphonium bromide. It was converted to hydrochloride by treating its ethereal solution with ethanolic hydrogen chloride.

Mass spectrum (m/z): 195, 110

IR absorption spectrum (neat) cm$^{-1}$: 2,980, 1,660, 1,078

NMR spectrum (DMSO-d$_6$; internal standard: TMS), δppm:

1.26(d, 3H, J = 5.9 Hz, ⟩CH—C$\underline{H}$$_3$), 1.40–1.90(m, 7H,

), 2.70(s, 3H, CH$_3$—N$\overset{+}{\underline{H}}$), 2.21–2.64(m, 6H, 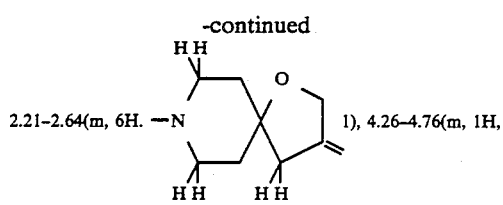), 4.26–4.76(m, 1H, \>CH—CH₃), 5.06–5.52(m, 1H, =C(H)(CH₃) )

EXAMPLE 18

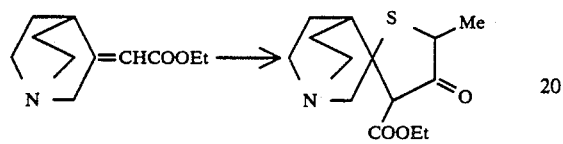

Ethyl 5′-methyl-4′-oxospiro[1-azabicyclo-[2.2.2]octane-3,2′-thiolan ]-3′-carboxylate was prepared in much the same manner as in Example 6, except that ethyl 3-quinuclidylideneacetate was used in place of ethyl 1-methyl-4-piperidylideneacetate.

Mass spectrum (m/z): 283, 237, 210

IR absorption spectrum (neat) cm⁻¹: 2,948, 1,748, 1,728

NMR spectrum (CDCl₃; internal standard: TMS), δppm:

1.20–1.56(m, 6H, —COOCH₂CH₃, \>CHCH₃), 1.5–2.2(m, 5H, 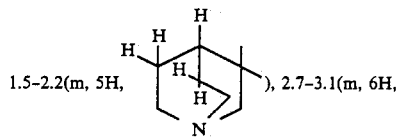), 2.7–3.1(m, 6H, \>N—CH₂— × 3) 4.0–4.2(m, 3H, \>CHCH₃,

—COO—CH₂—CH₃)

EXAMPLE 19

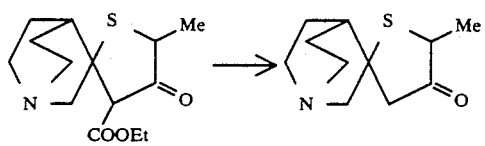

5′-methylspiro[1-azabicyclo[2.2.2]octane-3,2′-thiolan]-4′-one was prepared in much the same manner as in Example 2, and converted to its hydrochloride by treating its ethereal solution with ethanolic hydrochloride.

Melting point: 207–210° C. (dec.)

Mass spectrum (m/z): 211, 141, 122, 96

IR absorption spectrum (KBr) cm⁻¹: 3,464 (broad), 2,950, 2,480, 1,736

NMR spectrum (CDCl₃; internal standard: TMS), δppm:

1.42, 1.45(d × 2, 3H, J = 6.3 Hz, \>CHCH₃), 1.8–2.6(m, 5H, 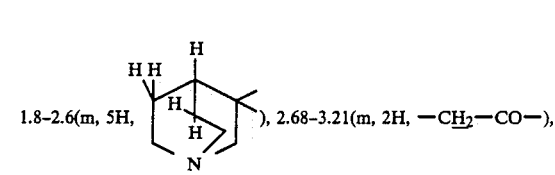), 2.68–3.21(m, 2H, —CH₂—CO—),

3 × 2–3.9(7H, \>NH⁺—CH₂— × 3, \>CHCH₃)

EXAMPLE 20

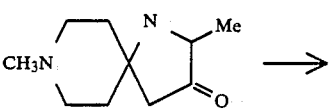

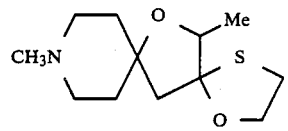

10, 14-Dimethyl-1,13-dioxa-4-thia-10-azadispiro[4.1.5.3]tetradecane was prepared in much the same manner as in Example 4, except that 2-mercaptoethanol was used in place of ethylene glycol. It was then converted to maleate by addition of an equimolar amount of maleic acid to its solution in isopropanol.

Mass spectrum (m/z): 243, 182, 156

IR absorption spectrum (neat) cm⁻¹: 2,950, 1,088, 1,058

NMR spectrum (CDCl₃; internal standard: TMS), δppm:

1.22, 1.24 (d × 2, 3H, J=5.9Hz, \>C—CH₃), 1.78–2.40 (m,

6H, —N 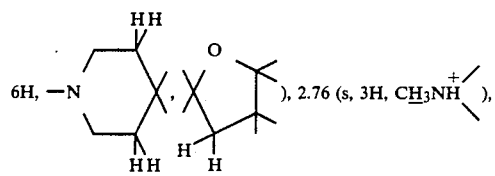), 2.76 (s, 3H, CH₃NH⁺\<), 2.68–3.52 (m, 6H, \>NH—CH₂— × 2, 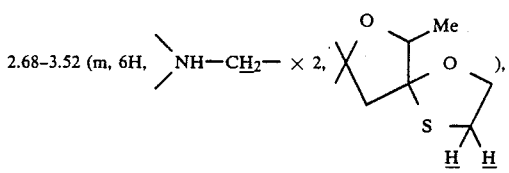), -continued 3.84–4.36 (m, 3H, 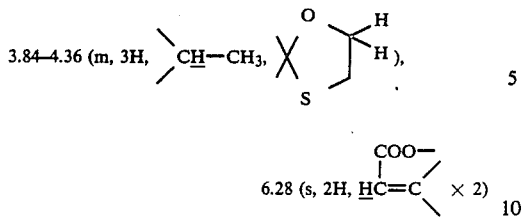), 6.28 (s, 2H, 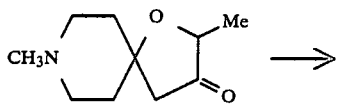 × 2)

EXAMPLE 21

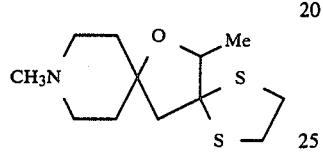

A solution of 0.5 g 2,8-diemthyl-1-oxa-8-azaspiro[4.5]-decan-3-one in 10 ml dichloromethane was cooled in ice, 0.45 ml 1,2-ethanedithiol was added, and 2 ml boron trifluoride/ether complex was then added dropwise while maintaining the temperature below 10° C. After stirring at that temperature for one hour, the reaction mixture was poured into 30 ml of 20% aqueous caustic soda solution. The insoluble matters were filtered off, the filtrate was extracted with ethyl acetate, and the organic layer was washed with saturated aqueous solution of sodium chloride and dried over anhydrous magnesium sulfate. The dried solution was concentrated under reduced pressure, and the residue was subjected to silica gel column chromatography using, as eluent, a mixed solvent of chloroform/methanol/conc. ammonia (20:1:0.1 by volume), giving 0.46 g of 10,14-dimethyl-13-oxa-1,4-dithia-10-azadispiro[4.1.5.2.]tetradecane. It was dissolved in methanol and converted to maleate by addition of an equimolar amount of maleic acid dissolved in the same solvent.

Melting point: 114–115° C.

Elemental analysis ($C_{16}H_{25}NO_5S_2$):

|  | C(%) | H(%) | N(%) | S(%) |
|---|---|---|---|---|
| Calcd. | 51.18 | 6.71 | 3.73 | 17.08 |
| Found | 50.87 | 6.57 | 3.66 | 17.28 |

Mass spectrum (m/z): 259, 231, 187

IR absorption spectrum (KBr) cm$^{-1}$: 2,940, 1,584, 1,092, 1,066

NMR spectrum (DMSO-d$_6$; internal standard: TMS), δppm:

1.23 (d, 3H, J=5.9Hz, \C—CH$_3$), 1.60–2.04 (m, 4H,

-continued

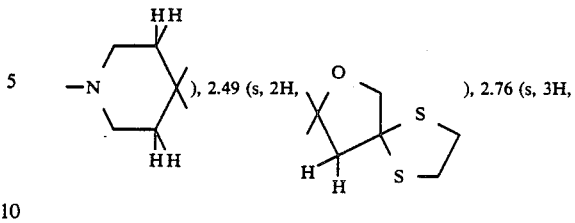), 2.49 (s, 2H, ), 2.76 (s, 3H,

CH$_3$—$\overset{+}{\text{NH}}$ ), 3.00–3.42 (m, 8H, \$\overset{+}{\text{NH}}$—CH$_2$— × 2, —S—CH$_2$— × 2), 4.06 (q, 1H, J=5.9Hz, \CH—CH$_3$), 6.03 (s, 2H, 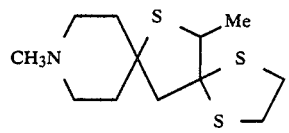 × 2)

EXAMPLE 22

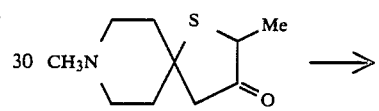

10,14-Dimethyl-1,4,13-trithia-10-azadispiro[4.1.5.2]-tetradecane was prepared in much the same manner as in Example 21 by using 2,8-dimethyl-1-thia-8-azaspiro[4.5]decan-3-one. It was then dissolved in isopropanol and converted to maleate by addition of an equimolar amount of maleic acid dissolved in the same solvent.

Mass spectrum (m/z): 275, 242, 110

IR absorption spectrum (KBr) cm$^{-1}$: 3,460 (broad), 2,950, 1,582, 1,472

NMR spectrum (CDCl$_3$; internal standard: TMS), δppm:

1.40 (d, 3H, J=6.5Hz, \C—CH$_3$), 2.4–2.8 (m, 2H,

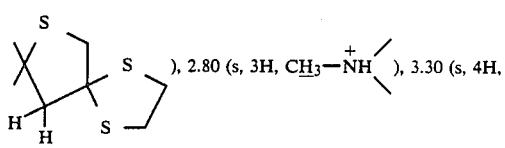), 2.80 (s, 3H, CH$_3$—$\overset{+}{\text{NH}}$ ), 3.30 (s, 4H,

—S—CH$_2$— × 2), 3.69 (q, 1H, J=6.5Hz, \CH—CH$_3$), 1.9–3.5 (8H other than the above), 6.28 (s, 2H, 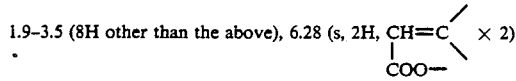 × 2)

EXAMPLE 23

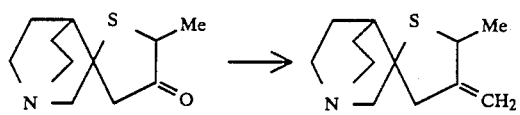

5'-Methyl-4'-methylenespiro[1-azabicyclo[2.2.2]-octane-3,2'-thiolane] was prepared in much the same manner as in Example 5 by using 5'-methylspiro[1-azabicyclo[2.2.2]-octane-3,2'-thiolan]-4'-one. It was dissolved in ethanol, and then convereted to hydrochloride by addition of ethanolic hydrogen chloride.

Melting point: 164–168° C.
Elemental analysis ($C_{12}H_{20}NSCl.0.1H_2O$):

|  | C(%) | H(%) | N(%) | S(%) |
|---|---|---|---|---|
| Calcd. | 58.21 | 8.22 | 5.66 | 12.94 |
| Found | 58.11 | 7.96 | 5.92 | 12.94 |

Mass spectrum (m/z): 209, 176, 139, 96
IR absorption spectrum (KBr) cm$^{-1}$: 3,480 (broad), 2,930, 2,580, 1,655
NMR spectrum (CDCl$_3$; internal standard: TMS), δppm:

1.42, 1.44 (d × 2, 3H, J=6.3Hz, 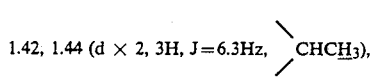), 1.8–2.5 (m, 5H, 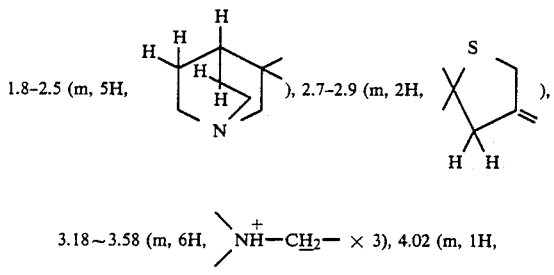), 2.7–2.9 (m, 2H, 3.18~3.58 (m, 6H, \NH$^+$—C$\underline{H}_2$— × 3), 4.02 (m, 1H, \C$\underline{H}$—CH$_3$), 4.88–5.10 (m, 2H, \>=CH$_2$) 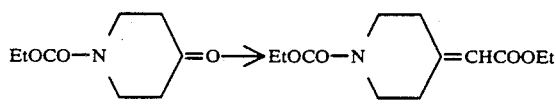

REFERENCE EXAMPLE 3

EtOCO—N⟨⟩=O ⟶ EtOCO—N⟨⟩=CHCOOEt

To a suspension of 4 g oily sodium hydride (60%) in 200 ml of anhydrous 1,2-dimethoxyethane, was added dropwise 23.6 g ethyl diethylphosphonoacetate at about 20° C., and the mixture was stirred at that temperature for about one hour. To the solution thus obtained, was added dropwise 17.1 g N-ethoxycarbonyl-4-piperidone at temperatures below 30° C., the mixture was stirred for an additional two hours, and the solvent was distilled off under reduced pressure. Ice water (100 ml) and ethyl acetate (100 ml) were added to the residue, the mixture was shaken, and the layers were separated. The aqueous layer was extracted twice with 100 ml ethyl acetate, and all the organic solutions were combined, washed with water and dried over anhydrous magnesium sulfate. Distilling off the solvent from the dried solution gave 25.7 g of ethyl N-ethoxycarbonyl-4-piperidylideneacetate as colorless solid.

Mass spectrum (m/z): 241, 212, 196, 168
IR absorption spectrum (KBr) cm$^{-1}$: 2,990, 1,718, 1,686
NMR spectrum (CDCl$_3$; internal standard: TMS), δppm:

1.28 (t × 2, 6H, J=7.2Hz, —OCH$_2$C$\underline{H}_3$ × 2), 2.3 (m, 2H, 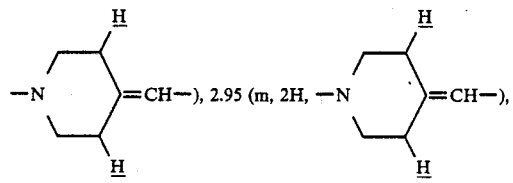=CH—), 2.95 (m, 2H, —N⟨⟩=CH—), 3.55 (m, 4H, 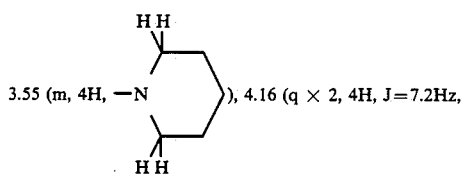), 4.16 (q × 2, 4H, J=7.2Hz, —OC$\underline{H}_2$CH$_3$ × 2), 5.72 (m, 1H, 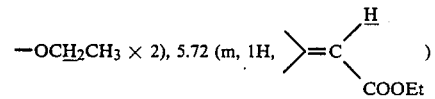)

EXAMPLE 24

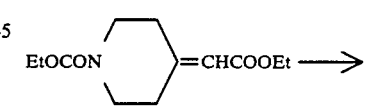

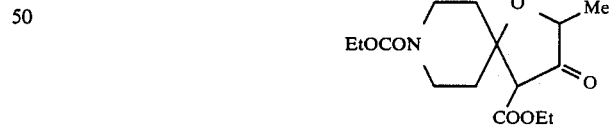

Ethyl 8-ethoxycarbonyl-2-methyl-3-oxo-1-oxa-8-azaspiro-[4.5]decane-4-carboxylate (oil) was prepared in much the same manner as in Example 1.

Mass spectrum (m/z): 313, 284, 268, 239
IR absorption spectrum (neat) cm$^{-1}$: 2,990, 1,776, 1,738, 1,704
NMR spectrum (CDCl$_3$; internal standard: TMS), δppm:

1.18–1.50 (m, 9H, \CH—CH$_3$, —OCH$_2$C$\underline{H}_3$ × 2), 1.5–2.1 (m,

EXAMPLE 25

EtOCO—N⟨spiro⟩(COOEt)(=O)(O)-Me → EtOCO—N⟨spiro⟩(O)(=O)-Me

To a solution of 2.74 g ethyl 8-ethoxycarbonyl-2-methyl-3-oxo-1-oxa-8-azaspiro[4,5]decane-4-carboxylate in 10 ml N,N-dimethylformamide, were added 512 mg sodium chloride and 315 μl water, and the mixture was heated with stirring for two hours in an oil bath held at 140–150° C. The reaction mixture was poured into 30 ml ice water, the resulting mixture was extracted with chloroform, and the extract was washed with an aqueous solution of sodium chloride and dried over anhydrous magnesium sulfate. After distilling off the solvent from the dried solution, the residue was purified by silica gel column chromatography using, as eluent, a mixed solvent of n-hexane/ethyl acetate (1:1 by volume), giving 1.54 g of 8-ethoxycarbonyl-2-methyl-1-oxa-8-azaspiro[4,5]-decan-3-one as oil.

Mass spectrum (m/z): 241, 212, 196, 140

IR absorption spectrum (neat) cm$^{-1}$: 2,990, 2,960, 1,764, 1,700

NMR spectrum (CDCl$_3$; internal standard: TMS), δppm:

1.28 (t, 3H, J=7.2Hz, —OCH$_2$CH$_3$), 1.32 (d, 3H, J=7.2Hz, ⟩CHCH$_3$), 1.50–1.90 (m, 4H, piperidine-H), 2.30 (s, 2H, —CH$_2$—CO—), 3.28–3.90 (m, 4H, piperidine-H), 4.03 (q, 1H, J=7.2Hz, ⟩CHCH$_3$), 4.15 (q, 2H, J=7.2Hz, —OCH$_2$CH$_3$)

EXAMPLE 26

EtOCO—N⟨spiro⟩(O)(=O)-Me → EtOCO—N⟨spiro⟩(O)(OH)-Me

8-Ethoxycarbonyl-3-hydroxy-2-methyl-1-oxa-8-azaspiro-[4.5]decane (oil) was prepared in much the same manner as in Example 3 and purified by silica gel column chromatography using, as eluent, a mixed solvent of ethyl acetate/n-hexane (1:1 by volume).

Mass spectrum (m/z): 244 (M+1), 225, 198

IR absorption spectrum (KBr) cm$^{-1}$: 3,464 (broad), 2,948, 1,682

NMR spectrum (CDCl$_3$; internal standard: TMS), δppm:

1.20–1.36 (m, 6H, ⟩CHCH$_3$, —OCH$_2$CH$_3$), 1.50–2.24 (m, 6H, piperidine/spiro-H), 3.28–3.80 (m, 4H, piperidine-H), 3.84–4.30 (m, 4H, —OCH$_2$CH$_3$, ⟩CHCH$_3$, ⟩CH(OH))

EXAMPLE 27

EtOCO—N⟨spiro⟩(O)(OH)-Me → EtOCO—N⟨spiro⟩(O)(OMe)-Me

A solution of 93 mg 8-ethoxycarbonyl-3-hydroxy-2-methyl-1-oxa-8-azaspiro[4.5]decane in 1 ml N,N-dimethylforamide was cooled in ice, 16.7 mg oily sodium hydride (60%) was added, and the resulting mixture was stirred for 30 minutes under ice cooling. Methyl iodide (26.2 μl) was then added, and the mixture was stirred at room temperature for about 24 hours and poured into 5 ml ice water. After extraction with chloroform, the extract was washed with an aqueous solution of sodium chloride and dried over anhydrous magnesium sulfate. The solvent was distilled off under reduced pressure from the dried solution, and the residue was purified by silica gel column chromatography using, as eluent, a mixed solvent of ethyl acetate/n-hexane (1:1 by volume), giving 47 mg 8-ethoxycarbonyl-3-methoxy-2-methyl-1-oxa-8-azaspiro[4,5]decane as oil.

Mass spectrum (m/z): 257, 225, 180, 154

IR absorption spectrum (KBr) cm$^{-1}$: 2,990, 2,950, 1,704, 1,242

NMR spectrum (CDCl$_3$; internal standard: TMS), δppm:

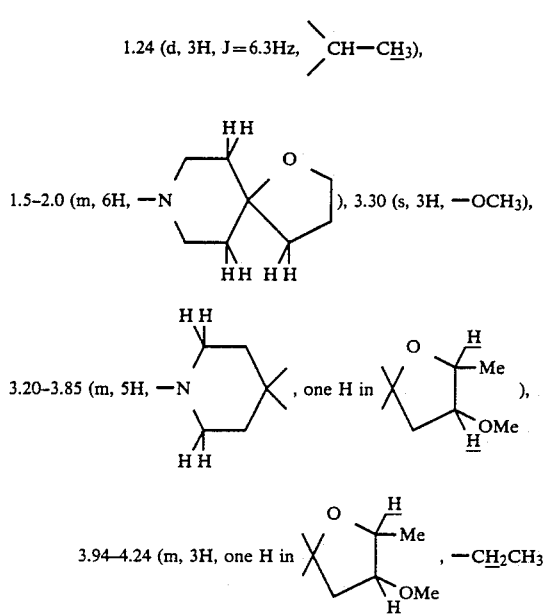

EXAMPLE 28

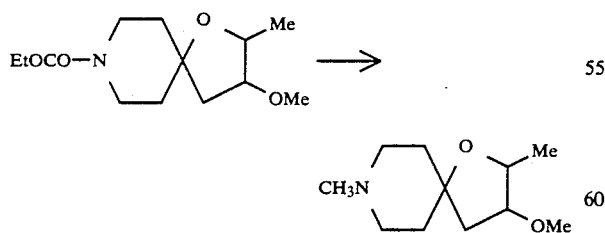

A suspension of 1.05 g lithium aluminum hydride in 35 ml anhydrous tetrahydrofuran was cooled to 0° C., 0.92 ml of 100% sulfuric acid was added dropwise while maintaining the temperature in the range from 0 to 7° C., and the mixture was stirred for 30 minutes in the above temperature range. A tetrahydrofuran solution (7 ml) containing 711 mg 8-ethoxycarbonyl-3-methoxy-2-methyl-1-oxa-8-azaspiro[4,5]-decane was then added, and stirring was continued at that temperature for one hour. Ether (35 ml) was then added, sodium sulfate decahydrate (2.6 g) was further added in small portions, and stirring was continued for an additional one hour. The white suspension thus obtained was filtered using perlite as filter aid, and the filter cake was washed with a mixed solvent of ethanol/chloroform (1:5). The washings were joined to the filtrate, the combined solution was concentrated under reduced pressure, and the residue was dissolved in chloroform. This solution was dried over anhydrous magnesium sulfate, chloroform was distilled off under reduced pressure, and the residue was purified by silica gel column chromatography using, as eluent, a mixed solvent of chloroform/methanol/conc. ammonia (10:1:0.1 by volume), giving 400 mg 3-methoxy-2,8-dimethyl-1-oxa-8-azaspiro[4.5]decane as oil. It was converted to hydrochloride by addition of ethanolic hydrogen chloride to its ethereal solution.

Mass spectrum (m/z): 199, 184, 168, 110

IR absorption spectrum (KBr) cm$^{-1}$: 3,480 (broad), 2,960, 2,675, 1,640, 1,475, 1,100

NMR spectrum (DMSO-d$_6$; internal standard: TMS), δppm:

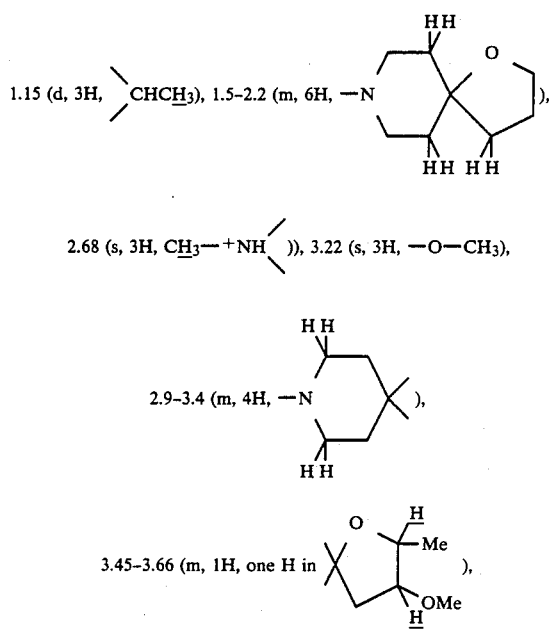

EXAMPLE 29

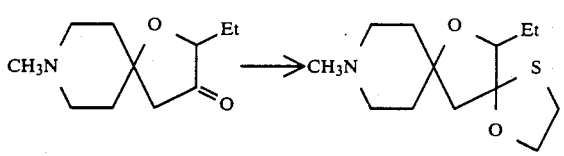

A solution (32 ml) of 0.53 g 2-ethyl-8-methyl-1-oxa-8-azaspiro[4.5]decan-3-one in dichloromethane was cooled in ice, 384 μl 2-mercaptoethanol and 2.05 ml boron trifluoride/ether complex were added in that order in an argon atmosphere, and the mixture was stirred at room temperature for 16 hours. The reaction mixture was poured into 23 ml of 20% aqueous solution of caustic soda, stirring was continued for about 15 minutes, and the two separate layers were collected. The aqueous layer was extracted with chloroform, the extract was joined to the organic layer separated above, and the combined solution was washed with saturated aqueous solution of sodium chloride and dried over anhydrous magnesium sulfate. The dried solution was concentrated under reduced pressure, and the residue was purified by silica gel column chromatography using, as eluent, a mixed solvent of chloroform/methanol/conc. ammonia (20:1:0.1 by volume), giving 460 mg of 14-ethyl-10-methyl-1,13-dioxa-4-thia-10-azadispiro[4,1,5,2]tetradecane as oil. It was then converted to maleate by treatment with maleic acid in isopropanol.

Mass spectrum (m/z): 257, 196, 110

NMR spectrum (CDCl$_3$; internal standard: TMS), δppm:

0.9–1.2 (m, 3H, \CH—CH$_2$—C$\underline{H}_3$), 1.5–2.3 (m, 8H, 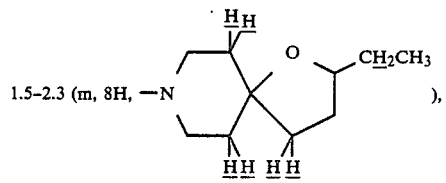 ), 2.78 (s, 3H, C$\underline{H}_3$+NH ), 2.95–3.5 (m, 6H, 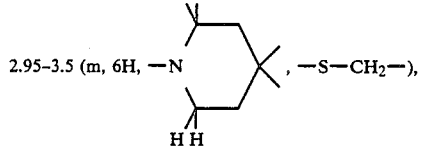, —S—CH$_2$—), 3.68–4.40 (m, 3H, 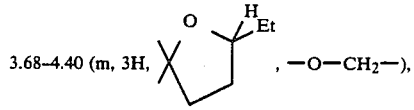, —O—CH$_2$—), 6.28 (s, 2H, 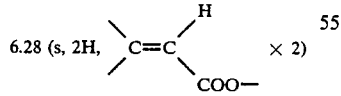 × 2)

EXAMPLE 30

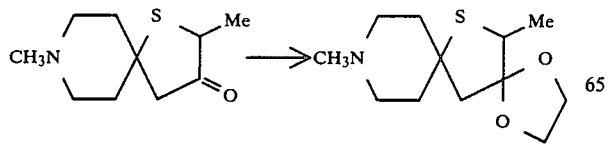

10,14-Dimethyl-1,4-dioxa-13-thia-10-azadispiro[4,1,5,2]-tetradecane was prepared and converted to maleate by treatment with maleic acid in isopropanol in much the same manner as in Example 4.

Melting point: 143–145° C.

Elemental analysis (C$_{16}$H$_{25}$NO$_6$S):

|  | C(%) | H(%) | N(%) | S(%) |
|---|---|---|---|---|
| Calcd. | 53.46 | 7.01 | 3.90 | 8.92 |
| Found | 53.21 | 6.86 | 3.74 | 8.94 |

Mass spectrum (m/z): 243, 210

NMR spectrum (CDCl$_3$; internal standard: TMS), δppm:

1.24 (d, 3H, J=7Hz, \C—C$\underline{H}_3$), 2.08–2.30 (m, 6H, 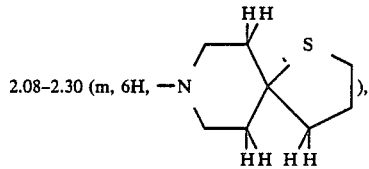 ), 2.76 (s, 3H, C$\underline{H}_3$+NH ), 2.70–3.10 (m, 2H, 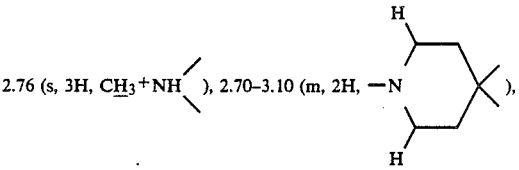 ), 3.30–3.60 (m, 3H, 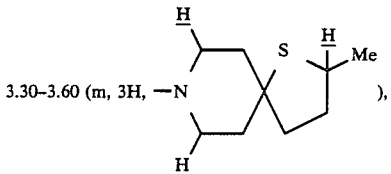 ), 4.0 (s, 4H, —O—CH$_2$— × 2), 6.18 (s, 2H, 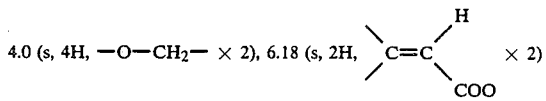 × 2)

EXAMPLE 31

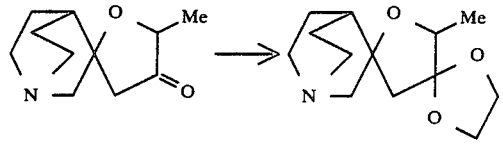

5'-Methyl-dispiro[1-azabicyclo[2,2,2]octane-3,2'-oxolane-4',2"-[1,3]dioxolane ] was prepared and converted to fumarate by treatment with fumaric acid in methanol in much the same manner as in Example 4.

Melting point: 158–159° C.

Elemental analysis (C$_{17}$H$_{25}$NO$_7$):

|  | C(%) | H(%) | N(%) |
|---|---|---|---|
| Calcd. | 57.45 | 7.09 | 3.94 |

-continued

| | C(%) | H(%) | N(%) |
|---|---|---|---|
| Found | 57.43 | 7.14 | 3.89 |

Mass spectrum (m/z): 239, 196, 139
NMR spectrum (DMSO-$d_6$; internal standard: TMS), δppm:

1.08 (d, 3H, 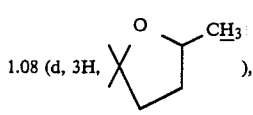), 1.4–2.4 (m, 7H, 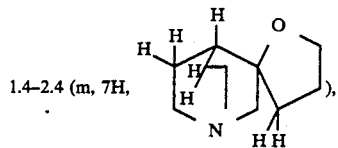), 2.8–3.3 (m, 6H, 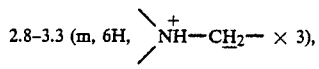), 3.75–4.05 (m, 5H, 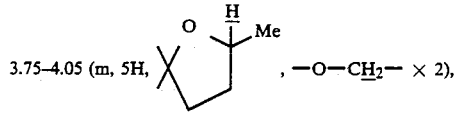), 6.48 (s, 2H, 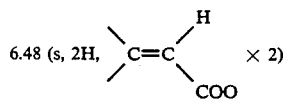 × 2)

EXAMPLE 32

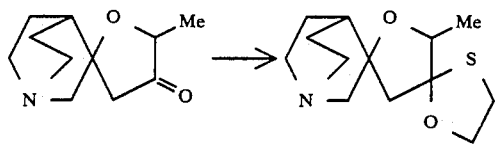

5'-Methyl-dispiro[1-azabicyclo[2,2,2]octane-3,2'-oxolane-4',2''-[1,3]oxathiolane ] was prepared and converted to fumarate by treatment with fumaric acid in methanol in much the same manner as in Example 29.

Melting point: 134–136° C.
Elemental analysis ($C_{17}H_{25}NO_6S$):

| | C(%) | H(%) | N(%) | S(%) |
|---|---|---|---|---|
| Calcd. | 54.97 | 6.78 | 3.77 | 8.63 |
| Found | 54.75 | 6.71 | 3.76 | 8.80 |

NMR spectrum (DMSO-$d_6$; internal standard: TMS), δppm:

1.15 (d, 3H, 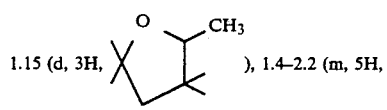), 1.4–2.2 (m, 5H,

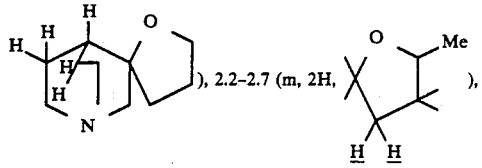), 2.2–2.7 (m, 2H, 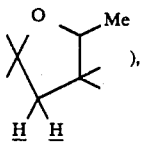), 2.8–3.4 (m, 8H, 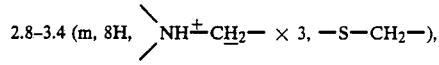), 3.85–4.40 (m, 3H, 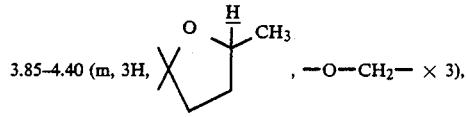), 6.48 (s, 2H, 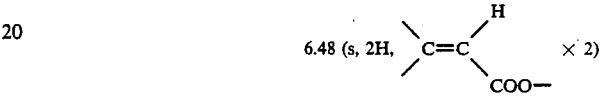 × 2)

EXAMPLE 33

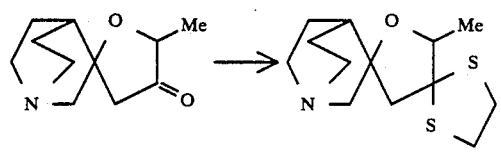

5'-Methyl-dispiro[1-azabicyclo[2,2,2]octane-3,2'-oxolane-4',2''-[1,3]dithiolane ] was prepared in the same manner as in Example 29, and subjected to silica gel column chromatography using, as eluent, a mixed solvent of chloroform/methanol, thus giving isomer A (fraction eluted earlier) and isomer B (fraction eluted later). Each of these isomers was converted to fumarate by treatment with fumaric acid in methanol (Physicochemical properties)

Fumarate of isomer A

Melting point: 184–186° C.
Elemental analysis ($C_{17}H_{25}NO_5S_2$):

| | C(%) | H(%) | N(%) | S(%) |
|---|---|---|---|---|
| Calcd. | 52.69 | 6.50 | 3.61 | 16.55 |
| Found | 52.56 | 6.37 | 3.58 | 16.55 |

Mass spectrum (m/z): 271, 238, 210
NMR spectrum (DMSO-$d_6$; internal standard: TMS), δppm:

1.27 (d, 3H, J=7Hz, 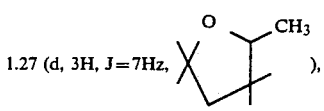), 1.5–2.2 (m, 5H, 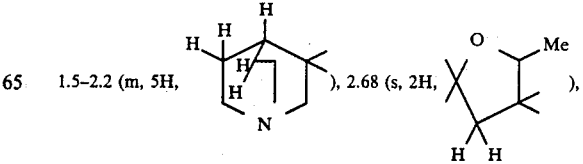), 2.68 (s, 2H, 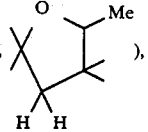), -continued 2.8-3.6 (m, 6H,  × 3), 3.3 (s, 4H,

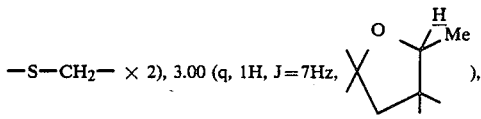—S—CH₂— × 2), 3.00 (q, 1H, J=7Hz, 6.48 (s, 2H, 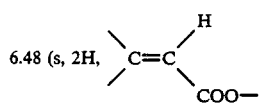 × 2)

Fumarate of isomer B

Melting point: 196-197° C.
Elemental analysis (C₁₇H₂₅NO₅S₂):

|  | C(%) | H(%) | N(%) | S(%) |
|---|---|---|---|---|
| Calcd. | 52.69 | 6.50 | 3.61 | 16.55 |
| Found | 52.47 | 6.42 | 3.52 | 16.59 |

Mass spectrum (m/z): 271, 238, 210
NMR spectrum (DMSO-d₆; internal standard: TMS), δppm:

1.24 (d, 3H, J=7Hz, 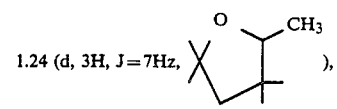), 1.5-2.2 (m, 5H, 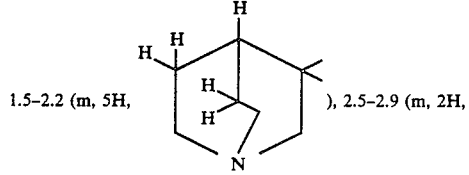), 2.5-2.9 (m, 2H,

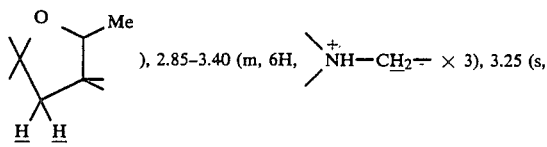), 2.85-3.40 (m, 6H, NH—CH₂— × 3), 3.25 (s,

4H, —S—CH₂— × 2), 4.08 (q, 1H, J=7Hz, 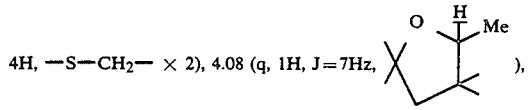), 6.48 (s, 2H, 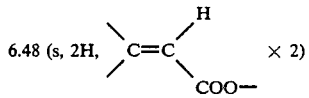 × 2)

EXAMPLE 34

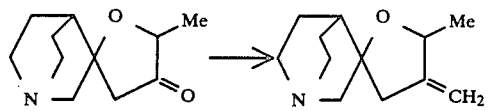

5′-Methyl-4′-methylenespiro[1-azabicyclo[2,2,2]octane-3,2′-oxolane] was prepared in much the same manner as in Example 5 and converted to fumarate by treatment with fumaric acid in methanol.

Melting point: 172-173° C.
Elemental analysis (C₁₆H₂₃NO₅):

|  | C(%) | H(%) | N(%) |
|---|---|---|---|
| Calcd. | 62.12 | 7.49 | 4.53 |
| Found | 62.08 | 7.53 | 4.44 |

Mass spectrum (m/z): 193, 96
NMR spectrum (DMSO-d₆; internal standard: TMS), δppm:

1.24 (d, 3H, J=7Hz, 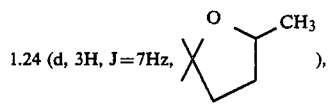), 1.40-2.30 (m, 5H, 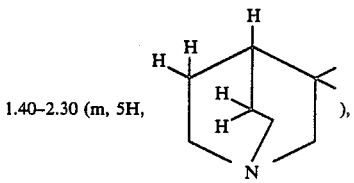), 2.35-3.00 (m, 2H, 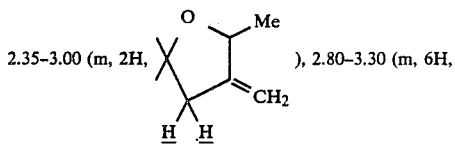), 2.80-3.30 (m, 6H, NH—CH₂— × 3), 4.20-4.60 (m, 1H, 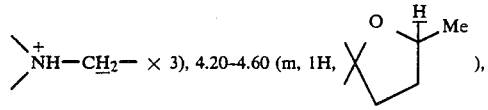), 4.90 (m, 1H, one H in 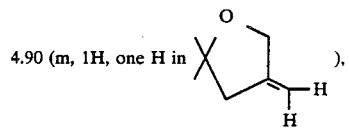), 5.01 (m, 1H, one H in 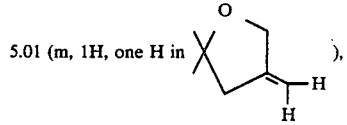), 6.48 (s, 2H, 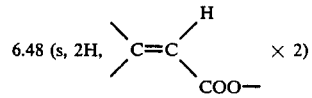 × 2)

EXAMPLE 35

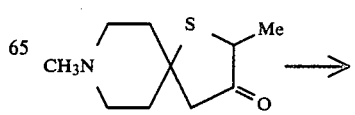

-continued 10,14-Dimethyl-1-oxa-4,13-dithia-10-azadispiro[4,1,5,2]tetradecane was prepared and converted to fumarate by treatment with fumaric acid in methanol in the same manner as in Example 29.

Melting point: 153–156° C.

Elemental analysis ($C_{16}H_{25}NO_5S_2$):

|  | C(%) | H(%) | N(%) |
|---|---|---|---|
| Calcd. | 51.18 | 6.71 | 3.73 |
| Found | 50.75 | 6.73 | 3.66 |

Mass spectrum (m/z): 259, 226, 198

NMR spectrum (DMSO-$d_6$; internal standard: TMS), δppm:

1.12–1.30 (d × 2, 3H, [S-CH(Me)-]), 1.6–2.10 (m, 4H, 2.0–2.5 (m, 2H, [piperidine NH]), 2.4–2.9 (m, 7H, $CH_3-\overset{+}{N}H$, $\overset{+}{N}H-CH_2- \times 2$), 2.9–3.1 (m, 2H, $-S-CH_2-$), 3.25–3.75 (q × 2, 1H, [S-CH(Me)]), 3.84–4.40 (m, 2H, $-OCH_2-$), 6.56 (s, 2H $\overset{\diagdown}{C}=\overset{\diagup}{C}$ × 2)
$\underset{COO}{\diagup}$ $\overset{\diagdown}{}$

EXAMPLE 36

2-Ethyl-8-methyl-3-methylene-1-oxa-8-azaspiro[4,5]-decane was prepared in much the same manner as in Example 5 and converted to hydrochloride by addition of ethreal hydrochloride to its solution in ethyl acetate.

Melting point: 142° C.

Elemental analysis ($C_{12}H_{22}NOCl$):

|  | C(%) | H(%) | N(%) | Cl(%) |
|---|---|---|---|---|
| Calcd. | 62.19 | 9.57 | 6.04 | 15.30 |
| Found | 61.80 | 9.47 | 5.94 | 15.15 |

Mass spectrum (m/z): 195, 96

IR absorption spectrum (KBr) cm$^{-1}$: 1,668

NMR spectrum (DMSO-$d_6$; internal standard: TMS), δppm:

0.90 (t, 3H, J=7.2Hz, [ethyl CH3]), 1.16–2.28 (m, 6H, 2.36–3.51 (m, 6H, N[piperidine]), 2.72 (s, 3H, $CH_3-\overset{+}{N}H$), 4.08–4.40 (m, 1H, [OCH]), 4.88–4.96 (m, 1H, one H in =CH2), 4.98–5.07 (m, 1H, one H in =CH2), 11.0 (br, 1H, $\underline{H}Cl$)

Preparation Examples

Tablets

A mixture of 0.5 part by weight of the compound of Example 5 and 4.5 part by weight of lactose is pulverized, and mixed uniformly with 47.1 part by weight of lactose, 22.5 part by weight of crystalline cellulose and 0.4 part by weight of magnesium stearate. The resultant mixture is compacted to form tablets of 75 mg/tablet.

Capsules

A mixture of 0.5 part by weight of the compound of Example 15 and 4.5 part by weight of lactose is pulverized, and mixed uniformly with 14.3 part by weight of lactose, 60 part by weight of corn starch and 2.0 part by weight of magnesium stearate. The resultant mixture is filled into gelatin hard capsules to provide a capsuled preparation of 210 mg/capsule.

We claim:
1. A compound of the formula:

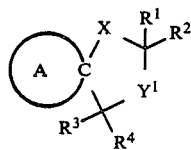    (I)

wherein

represents a piperidine ring of which the nitrogen atom may have substituent(s) selected from lower alkyl, lower alkanoyl or lower alkoxycarbonyl, and of which the nitrogen atom in the piperidine ring may be connected to any position carbon (which is not the common carbon atom of the spiro structure) via lower alkylene, X represents an oxygen atom,
Y represents a carbonyl group

, a thiocarbonyl group

, a group of the formula >CH—$R^5$, a group of the formula

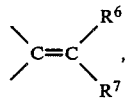, or a group of the formula

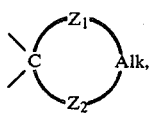

$R^1$, $R^2$ and $R^3$, which are the same or different, each represents a hydrogen atom or a lower alkyl group,
$R^4$ represents a hydrogen atom, a lower alkyl group, a carboxy group, a lower alkoxycarbonyl, or a lower alkanoyl,
$R^5$ represents a halogen atom, a hydroxyl group, a mercapto group, a lower alkoxy group, a lower alkylthio group, a lower alkanoyloxy group, or a lower alkanoylthio group, $R^6$ and $R^7$, which are the same or different, each represents a hydrogen atom or a lower alkyl group,
$Z_1$ and $Z_2$, which are the same or different, each represents an oxygen atom or a sulfur atom,
Alk represents a lower alkylene group; or a salt of the formula (I) compound, with the proviso that when

represents methylpiperidyl, $R^2$–$R^4$ represent hydrogen, $R^1$ represents lower alkyl, then Y does not represent carbonyl or vinylidene.

2. The compound of claim 1 wherein

represents a piperidine ring in which the nitrogen atom is substituted with a lower alkyl group.

3. The compound of claim 1 wherein Y represents a carbonyl group.

4. The compound of claim 1 wherein Y represents a thiocarbonyl group.

5. The compound of claim 1 wherein Y represents >CH—$R^5$.

6. The compound of claim 1 wherein Y represents

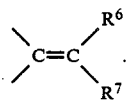

7. The compound of claim 1 wherein Y represents

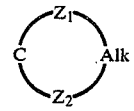

8. The compound of claim 1 wherein X represents oxygen and

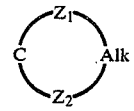

represents a piperidine ring in which the nitrogen atom is substituted with a lower alkyl group.

9. A pharmaceutical composition useful for activating cholinergic function in the central nervous system, said composition comprised of from about 0.001 mg to about 500 mg of the compound of claim 1 and a pharmaceutically acceptable carrier.

* * * * *